(12) United States Patent
Schasteen et al.

(10) Patent No.: US 7,846,685 B2
(45) Date of Patent: Dec. 7, 2010

(54) METHODS AND COMPOSITIONS FOR THE CONTROL OF COCCIDIOSIS

(75) Inventors: Charles S. Schasteen, St. Louis, MO (US); Jackie Green, Lincoln, NE (US); Lance Bull, St. John, MO (US); Farooq Uraizee, Valley Park, MO (US); Mary Ann Pfannenstiel, Lincoln, NE (US); Tony Allington, Valparaise, NE (US); Steven J. Mueller, Ballwin, MO (US)

(73) Assignee: Novus International, Inc., St. Charles, MO (US)

( * ) Notice: Subject to any disclaimer, the term of this patent is extended or adjusted under 35 U.S.C. 154(b) by 1104 days.

(21) Appl. No.: 10/799,083

(22) Filed: Mar. 12, 2004

(65) Prior Publication Data

US 2004/0175391 A1    Sep. 9, 2004

Related U.S. Application Data

(62) Division of application No. 10/005,510, filed on Nov. 8, 2001, now abandoned.

(60) Provisional application No. 60/246,847, filed on Nov. 8, 2000.

(51) Int. Cl.
*C12P 1/00*    (2006.01)
*C12N 15/09*   (2006.01)
*A61K 39/00*   (2006.01)
*A61K 39/012*  (2006.01)

(52) U.S. Cl. .................. 435/41; 435/69.3; 424/184.1; 424/265.1; 424/271.1

(58) Field of Classification Search ............ 424/184.1, 424/151.1, 271.1; 530/300
See application file for complete search history.

(56) References Cited

U.S. PATENT DOCUMENTS 3,147,186 A    9/1964    Edgar (Continued)

FOREIGN PATENT DOCUMENTS

EP    0243548 A1    11/1987

(Continued)

OTHER PUBLICATIONS

Singh et al (Cereal Chemistry, 72(4):344-348, 1995).*

(Continued)

*Primary Examiner*—Vanessa L. Ford
(74) *Attorney, Agent, or Firm*—Polseinlli Shughart PC

(57) ABSTRACT

Methods are provided for the sporulation, sterilization and storage of coccidial oocyst which are characterized by an absence of the highly toxic chemical potassium dichromate. Also provided are compositions containing sporulated oocysts which are free of potassium dichromate.

16 Claims, 7 Drawing Sheets

U.S. PATENT DOCUMENTS

| | | | |
|---|---|---|---|
| 3,890,888 | A | 6/1975 | Verberne |
| 4,399,151 | A * | 8/1983 | Sjoerdsma et al. .......... 514/564 |
| 4,438,097 | A | 3/1984 | Shirley |
| 4,544,548 | A | 10/1985 | Davis et al. |
| 4,639,372 | A | 1/1987 | Murray et al. |
| 4,724,145 | A | 2/1988 | Murray et al. |
| 4,808,404 | A | 2/1989 | Bhogal |
| 5,055,292 | A | 10/1991 | McDonald et al. |
| 5,068,104 | A | 11/1991 | Bhogal et al. |
| 5,311,841 | A | 5/1994 | Thaxton |
| 6,019,985 | A | 2/2000 | Brown et al. |
| 6,891,024 | B2 | 5/2005 | Marsh |
| 6,998,126 | B2 | 2/2006 | Davelaar |
| 2003/0143717 | A1 | 7/2003 | Hutchins et al. |

FOREIGN PATENT DOCUMENTS

| | | | |
|---|---|---|---|
| EP | 0258045 | A2 | 3/1988 |
| EP | 0325359 | A1 | 7/1989 |
| EP | 0506211 | A1 | 9/1992 |
| RU | 2019189 | | 9/1994 |
| SU | 19884621763 | * | 12/1988 |
| SU | 1637882 | * | 3/1991 |
| WO | WO 94/16725 | A1 | 8/1994 |
| WO | WO 96/40233 | A1 | 12/1996 |
| WO | WO 96/40234 | A1 | 12/1996 |
| WO | WO 00/50072 | * | 8/2000 |
| WO | WO 00/50072 | A2 | 8/2000 |
| WO | WO 01/34187 | A2 | 5/2001 |
| WO | WO 03/020917 | A1 | 3/2003 |

OTHER PUBLICATIONS

Kimura et al (Journal of Protozoology Research, Jul. 2000, vol. 10, No. 3, pp. 155-165) (Abstract only).*

.Svensson et al (Veterinary Parasitology, vol. 69, Issues 3-4, May 1997, pp. 211-218).*

Jenkins, et al., "Protective Immunity against Coccidiosis Elicited by Radiation-Attenuated *Eimeria maxima* Sporozoites that are Incapable of Asexual Development," Avian Diseases, Jan.-Mar. 1993, 37(1), pp. 74-82.

LIVACOXR® Natural Way of Protection of Poultry from Coccidiosis, "LIVACOXR® Live attenuated coccidiosis vaccine for poultry; Technical Manual for Use in Commercial Broiler Operations", BIOPHARM, Research Institute of Biopharmacy and Veterinary Drugs, Autumn, 1996; pp. 3-11.

Long, P.L. et al., "A Guide to Laboratory Techniques Used in the Study and Diagnosis of Avian Coccidiosis," Folia Veterinaria Latina, 1976, vol. VI(3), pp. 201-217.

Ryley, J.F. et al., "Methods in coccisiosis research: separation of oocysts from faeces," Parasitology, 1976, vol. 73(3), pp. 311-326.

Schering-Plough Animal Health, Material Safety Data Sheet, "PARACOX," Aug. 2, 2000, pp. 1-5.

Sharma, N., "Response of the Fowl (*Gallus domesticus*) to Parenteral Administration of Seven Coccidial Species," Journal of Parasitology, 1964, 50(4), pp. 509-517.

Smith et al., "The Respiration of the Protozoan Parasite, *Eimeria ténella*," Journal of Parasitology, 1944, 30, pp. 295-302.

Smith et al, "A Rapid Technique for the Cleaning and Concentration of *Eimeria* Oocysts", Poultry Science, 1975, 54: 2081-2086.

Wagenbach, G.E. et al., "A Method for Purifying Coccidian Oocysts Employing Clorox and Sulfuric Acid-Dichromate Solution," Journal of Parasitology, 1966, vol. 52, p. 1222.

Watkins, et al., "The Effect of in Ovo Oocyst or Sporocyst Inoculation on Response to Subsequent Coccidial Challenge," Poul. Sci., Oct. 1995, 74(10), pp. 1597-1602.

Williams, R.B., "The development, efficacy and epidemiological aspects of Paracox™, a new coccidiosis vaccine for chickens," Mallinckrodt Veterinary, Ltd., (date unknown), pp. 1-16.

Wilson, et al., "Biochemistry of Sporulation in Oocysts of *Eimeria acervulina*," J. Protozool., (1961) 8(4), pp. 410-416.

* cited by examiner

METHODS AND COMPOSITIONS FOR THE CONTROL OF COCCIDIOSIS

CROSS-REFERENCE TO RELATED APPLICATIONS

This application is a divisional of pending application Ser. No. 10/005,510, filed Nov. 8, 2001, which claims the benefit of U.S. Provisional Application No. 60/246,847, filed Nov. 8, 2000, both of which are hereby incorporated by reference in their entirety.

BACKGROUND

Coccidiosis is a disease of various animals in which the intestinal mucosa is invaded and damaged by a protozoa of the subclass Coccidia. The economic effects of coccidiosis can be especially severe in the poultry industry where intensive housing of birds favors the spread of the disease. Infection by coccidial protozoa is, for the most part, species specific. Numerous species, however, can infect a single host. For example, there are seven species of coccidial protozoa which infect chickens, six of which are considered to be moderately to severely pathogenic.

The life cycle of the coccidial parasite is complex. For example, protozoa of the genera *Eimeria, Isospora, Cystoisospora*, or *Cryptosporidium* typically only require a single host to complete their life cycle, although *Cystoisospora* may utilize an intermediate host. Under natural conditions, the life cycle begins with the ingestion of sporulated oocysts from the environment. When sporulated oocysts are ingested by a susceptible animal, the wall of the sporulated oocyst is broken in order to release the sporocysts inside. In poultry, the release of the sporocyst is the result of mechanical disruption of the sporulated oocyst in the gizzard. Within the sporocysts, are the sporozoites which are the infective stage of the organism. In poultry, the breakdown of the sporocyst coat and release of the sporozoites is accomplished biochemically through the action of chymotrypsin and bile salts in the small intestine. Once released, the sporozoites invade the intestinal mucosa or epithelial cells in other locations. The site of infection is characteristic of the species involved. For example, in the genus *Eimeria, E. tenella* is localized in the ceca; *E. necatrix* is found in the anterior and middle portions of the small intestine; *E. acervulina* and *E. praecox* occur in the upper half of the small intestine; *E. brunetti* occurs in the lower small intestine, rectum, ceca, and cloaca; *E. mitis* is found in the lower small intestine, while *E. maxima* can be found in any of these physiological locations.

Once inside the host animals' cells, sporozoites develop into multinucleate meronts, also called schizonts. Each nucleus of the meront develops into an infective body called a merozoite which enters new cells and repeats the process. After a variable number of asexual generations, merozoites develop into either microgametocytes or macrogametes. Microgametocytes develop into many microgametes which, in turn, fertilize the macrogametes. A resistant coat then forms around the resulting zygotes. The encysted zygotes are called oocysts and are shed unsporulated in the feces. Infected birds may shed oocysts in the feces for days or weeks. Under proper conditions of temperature and moisture, the oocysts become infective through the process of sporulation. Susceptible birds then ingest the sporulated oocysts through normal pecking activities or ground/litter foraging and the cycle repeats itself. Ingestion of viable, sporulated oocysts is the only natural means of infection.

Infection with coccidial protozoa results in immunity so that the incidence of the disease decreases over time as members of the flock become immune. This self-limiting nature of coccidial infections is widely known in chickens and other poultry. The immunity conferred, however, is species specific such that introduction of another species of coccidial protozoa will result in a new disease outbreak.

The oocyst wall of coccidial protozoa provides a highly effective barrier for oocyst survival. Oocysts may survive for many weeks outside the host. In the laboratory, intact oocysts are resistant to extremes in pH, detergents, proteolytic, glycolytic, and lipolytic enzymes, mechanical disruption, and chemicals such as sodium hypochlorite and dichromate.

Two methods are currently used to control coccidiosis in poultry. The first involves control by chemotherapy. Numerous drugs are available for the control of coccidiosis in poultry. Because of the number of species which cause the disease, very few drugs are efficacious against all species, although a single drug may be efficacious against several species. In modern broiler chicken production, for example, administration of drugs to control coccidiosis is routine. The expense for preventative medication against coccidiosis represents a significant cost of production.

Two programs of drug administration are commonly used in the domestic poultry industry. The simplest is the continuous use of a single drug from day one following hatching until slaughter. The second program is to use shuttle or dual drug program which involves the use of two different drugs, one administered in the "starter" ration and a second drug administered in the "grower" ration. This second method is often preferred as a method to minimize development of drug resistant strains of Coccidia. Using either method, drugs used are typically rotated two to three times per year in order to minimize the development of resistant strains.

The development of drug resistance by Coccidia is a serious limitation on the effectiveness of chemotherapy to control the disease. Surveys in the United States, South America and Europe have revealed widespread drug resistance in Coccidia. Since drug resistance is a genetic phenomenon, once established, drug resistance can remain in the population for many years until reduced by natural selection pressure and genetic drift.

The use of drugs in animals used for food production is also coming under increasing scrutiny by the public. Consumers are increasingly concerned with the possibility of drug residues in food. This creates pressure in the poultry industry to reduce the use of drugs to control coccidiosis.

Vaccination of birds against coccidiosis is an alternative to chemotherapy. An advantage of vaccination is that it can greatly reduce or eliminate the need to administer anti-coccidial drugs, thus reducing drug costs to poultry producers, preventing the development of drug-resistant strains, and lessening consumer concerns about drug residues.

Numerous methods have been developed to immunize poultry against coccidial protozoa. The successful methods have all been based on the administration of live protozoa, either fully virulent strains or attenuated strains. The most common route of administration is oral, although other routes have been used. Edgar, U.S. Pat. No. 3,147,186, teaches vaccination of chickens by oral administration either directly into the mouth or via the feed or water of viable *E. tenella* sporulated oocysts. Davis et al., U.S. Pat. No. 4,544,548, teaches a method of vaccination by continuous administration of low numbers of sporulated oocysts, with or without simultaneous administration of anti-coccidial drugs.

Oral administration of attenuated strains of sporocysts has also been utilized to confer immunity against coccidiosis.

Shirley, U.S. Pat. No. 4,438,097; McDonald, U.S. Pat. No. 5,055,292; and Schmatz et al., PCT publication No. WO 94/16725. An alternative to attenuation is disclosed in Jenkins et al., *Avian Dis.*, 37(1):74-82 (1993), which teaches the oral administration of sporozoites that have been treated with gamma radiation to prevent merogonic development.

Parenteral routes of vaccination have included subcutaneous or intraperitoneal injection of excysted sporozoites, Bhogal, U.S. Pat. No. 4,808,404; Bhogal et al., U.S. Pat. No. 5,068,104, and intra ovo injection of either oocysts or sporocysts, Evans et al., PCT publication No. WO 96/40233; Watkins et al., *Poul. Sci.*, 74(10):1597-602 (1995). Sharma, *J. Parasitol.*, 50(4):509-517 (1964), reported unsuccessful immunization trials involving intravenous, intraperitoneal, intramuscular, or subcutaneous injection of either viable oocysts or a mixture of oocysts, sporocysts and sporozoites. Thaxton, U.S. Pat. No. 5,311,841, teaches a method of vaccination against Coccidia by administration of oocysts or sporozoites to newly hatched chicks by yolk sac injection.

Regardless of the route of administration, procedures for the production of coccidiosis vaccines are quite similar. Briefly, coccidial protozoa are produced by infecting host animals with a single species of coccidial protozoa. These "seed stocks" are often clonal in nature, that is, derived from a single organism in order to insure the presence of only the species of interest. Seed stocks may be wild type, that is, isolated from the field, or they may be precocious or attenuated strains. The protozoa are then allowed to undergo replication in the host, after which, protozoa are collected from the animals, usually from the excreta. The use of attenuated strains typically results in fewer shed oocysts from the host animal. The protozoa are then separated from the excreta by well known techniques such as salt floatation and centrifugation. At the time of collection, the protozoa are at the non-infective oocyst stage of the life cycle. In order to become infective, and therefore useful for vaccines, the oocysts must be induced to undergo sporulation. In members of the genus *Eimeria*, sporulation typically involves the incubating the oocysts in a 1% to 4% aqueous solution of potassium dichromate at 19° C. to 37° C. with constant aeration. Data on oxygen consumption are conflicting, with Smith and Wilson (*J. Parasitol.* 30:295-302, 1944) reporting increased oxygen consumption for *E. tenella* and Wilson and Fairbairn (*J. Protozool.* 8:410-416, 1961) reporting no change in oxygen consumption for *E. acervulina*. Sporulation is usually complete within 12 to 24 hours depending on the temperature used. Monitoring of the sporulation process is accomplished by microscopic examination of the protozoa. Storage compositions found in the prior art typically include an aqueous solution of potassium dichromate. The sporulated oocysts are usually stored in 1 to 4% aqueous solution of potassium dichromate to prevent bacterial growth, however, other storage media have been used.

Current vaccines available for the prevention of coccidiosis typically contain a 2.5% weight to volume solution and contain approximately 1,600 oocyts per dose (400 sporulated oocysts representing four different species). The current commercially available vaccines contain from about $1.6 \times 10^{-2}$ µg of potassium dichromate per oocyst to about 0.16 µg of potassium dichromate per oocyst.

Although widely used for sporulation and storage, potassium dichromate has several properties which make its elimination from biologicals highly desirable. Potassium dichromate is a strong oxidizer and has been reported to affect the respiratory system, liver, kidneys, eyes, skin and blood. It is a known carcinogen and upon disposal is regarded as a hazardous waste. Because of its high toxicity, compounds containing potassium dichromate are particularly unsuitable for parenteral administration. Thus, it would be highly advantageous to eliminate potassium dichromate from the production and storage of materials to be administered to animals, especially food animals.

SUMMARY

Coccidiosis is a disease of animals which has a significant economic impact, especially in the poultry industry. In many poultry operations, birds are vaccinated against coccidiosis using vaccines containing sporulated oocysts. Present methods for the sporulation and storage of coccidial oocysts use the highly toxic chemical potassium dichromate. The present invention provides a method for the sporulation, sterilization and storage of coccidial oocysts, without the use of potassium dichromate. The present invention also provides for vaccine compositions that can be administered to animals, particularly from the class Aves, and more particularly poultry, said vaccines being characterized as substantially free of potassium dichromate, both in terms of their production and storage. Due to its high toxicity, the elimination of potassium dichromate is particularly desirable in the production and storage of compositions to be administered to animals, and in particular to food producing animals. As the vaccine compositions of the present invention are sterile, the vaccine compositions can be administered to animals, through various routes, including, but not limited to orally, e.g, by addition to food or water; topically, e.g., spraying; parenteral routes, e.g. subcutaneous, intramuscular or intraperitoneal injection; per os or via intra-yolk sac injection.

As used herein, the term substantially free of alkali metal dichromate indicates that no alkali metal dichromate is added to the composition during production, including the sporulation and storage of said composition. Furthermore, as used herein, the term substantially free of potassium dichromate indicates that no potassium dichromate is added to the composition during production, including the sporulation and storage of said composition.

The present invention provides a method for isolating oocysts, concentrating oocysts, sporulating oocysts, isolating sporulated oocysts, sterilizing sporulated oocysts and storage of sporulated oocysts. More particularly, the present invention provides a method for sporulating oocysts, isolating sporulated oocysts, sterilizing sporulated oocysts and storage of sporulated oocysts.

Among the several aspects of the invention, is provided a vaccine for the prevention and/or control of coccidiosis comprising viable sporulated oocysts of at least one species of protozoa known to cause coccidiosis, wherein the composition is sterile and characterized as substantially free of potassium dichromate.

Another aspect provides a vaccine for the prevention and/or control of coccidiosis comprising an aqueous diluent and viable sporulated oocysts of at least one species of protozoa known to cause coccidiosis wherein the vaccine is sterile and characterized as substantially free of potassium dichromate.

Another aspect of the invention provides a method of isolating and concentrating oocysts to prepare the oocysts for sporulation comprising a novel combination of isolation, cleansing, and concentration steps. The methods of the instant invention may be used individually or in combination with one another.

The method of isolating and concentrating oocysts comprises sieving a manure slurry known to contain oocysts. The method further comprises concentrating the oocysts by centrifugal-based separation. The method further comprises a flotation step to further cleanse and isolate the oocysts. The method further comprises centrifugal-based separation, followed by a flotation step, followed by another application of centrifugal-based separation.

Another aspect provides a method for isolating oocysts comprising collecting feces that contains oocysts known to cause coccidiosis. The feces are contacted with an aqueous medium, and unwanted fecal matter is separated from the oocysts. The oocysts are subjected to centrifugal-based separation and the solid oocyst-containing fraction is collected and suspended in a flotation solution. The oocysts are allowed to separate from the solids, and the flotation medium is removed from the oocysts by tangential flow filtration.

A further aspect provides a method for inducing the sporulation of oocysts comprising incubating viable oocysts of at least one species of protozoa known to cause coccidiosis in an aqueous medium wherein dissolved oxygen concentration is maintained from about 30% to about 80% of saturation. Temperature is controlled from a temperature which prevents substantial freezing up to about 43° C. An oxidizing agent, other than potassium dichromate, is added at a sporulation inducing concentration to form a sporulation medium; and the sporulation medium is incubated to form sporulated oocysts.

Another aspect provides a method for inducing the sporulation of oocysts comprising incubating viable oocysts of at least one species of protozoa known to cause coccidiosis in an aqueous medium wherein dissolved oxygen concentration is maintained at at least about 50% of saturation. Temperature is controlled from a temperature which prevents substantial freezing up to 43° C. An oxidizing agent, other than an alkali metal dichromate, soluble dichromate moieties, dichromate ions, or potassium dichromate, to form a sporulation medium; and wherein the oxidizing agent is at a sporulation inducing concentration. The sporulation medium is then incubated to form sporulated oocysts; the sporulated oocysts are then separated from the sporulation medium; the sporulated oocysts are then sterilized with a chemical disinfectant; the chemical disinfectant is removed by tangential flow filtration. The sporulated oocysts may then be stored in a diluent substantially free of potassium dichromate as it has been discovered that an oxidizing agent, other than dissolved oxygen available in sterile water, is not necessary to preserve viability for useful periods of time. However, the use of an oxidizing agent may increase longevity of the vaccine, and thus, may be used as part of the instant invention.

Another aspect provides a method for sporulating oocysts comprising incubating oocysts of at least one species of protozoa known to cause coccidiosis in an aqueous sporulation medium, and separating the oocysts by tangential flow filtration from the sporulation medium.

Yet another aspect provides a method for sterilizing oocysts comprising contacting oocysts of at least one species of protozoa known to cause coccidiosis with a sterilization medium, and removing the sterilization medium from the oocysts by tangential flow filtration.

Still a further aspect provides, a method for monitoring sporulation of oocysts comprising, incubating viable oocysts in a medium under sporulation inducing conditions, and monitoring the medium during the incubation for a change in pH, or a change in the combination of dissolved oxygen and pH, the change being characteristic of sporulation.

Yet another aspect provides, a kit for the prevention and/or control of coccidiosis comprising a vaccine comprising sterile, viable, sporulated oocysts of at least one species of protozoa known to cause coccidiosis, the vaccine being characterized as substantially free of potassium dichromate; and instructions for administering the composition to an animal. In another embodiment, the kit further comprises a diluent, which may be sterile, and instructions for mixing the oocysts with the diluent to form a mixture and for administering the mixture to an animal.

Another aspect provides, a composition for the storage of sporulated oocysts comprising an aqueous diluent and a bactericide, the composition being sterile and being characterized as substantially free of potassium dichromate. In yet another embodiment the aqueous diluent comprises water. In a further embodiment the aqueous diluent comprises domestic water. In a further embodiment the aqueous diluent comprises from about 0.1× to about 1× phosphate buffered saline (PBS) and from about 0 to about 30 µg/ml gentamicin.

A further aspect provides, a method for storing sporulated oocysts comprising obtaining sterile, sporulated oocysts of at least one species of protozoa known to cause coccidiosis and placing the sporulated oocysts in a composition comprising an aqueous diluent and a bactericide, the composition being sterile and being characterized as substantially free of added potassium dichromate.

Yet another aspect provides, a method for storing sporulated oocysts comprising obtaining sterile, sporulated oocysts of at least one species of protozoa known to cause coccidiosis; placing the sporulated oocysts in a sterile composition comprising 0.5×PBS and about 30 µg/ml gentamicin, the composition being characterized as substantially free of potassium dichromate; and storing the composition containing the sporulated oocysts at less than about 10° C., preferably between about 1° C. to about 8° C., more preferably from about 3° C. to about 6° C., and most preferably, about 4° C.

In yet another aspect, the invention provides a combination of species of oocysts from the genus *Eimeria* comprising a minimum immunizing dose of oocysts.

BRIEF DESCRIPTION OF THE DRAWINGS

These and other features, aspects, and advantages of the present invention will become better understood with regard to the following description, appended claims and accompanying figures where:

Figure 1A:
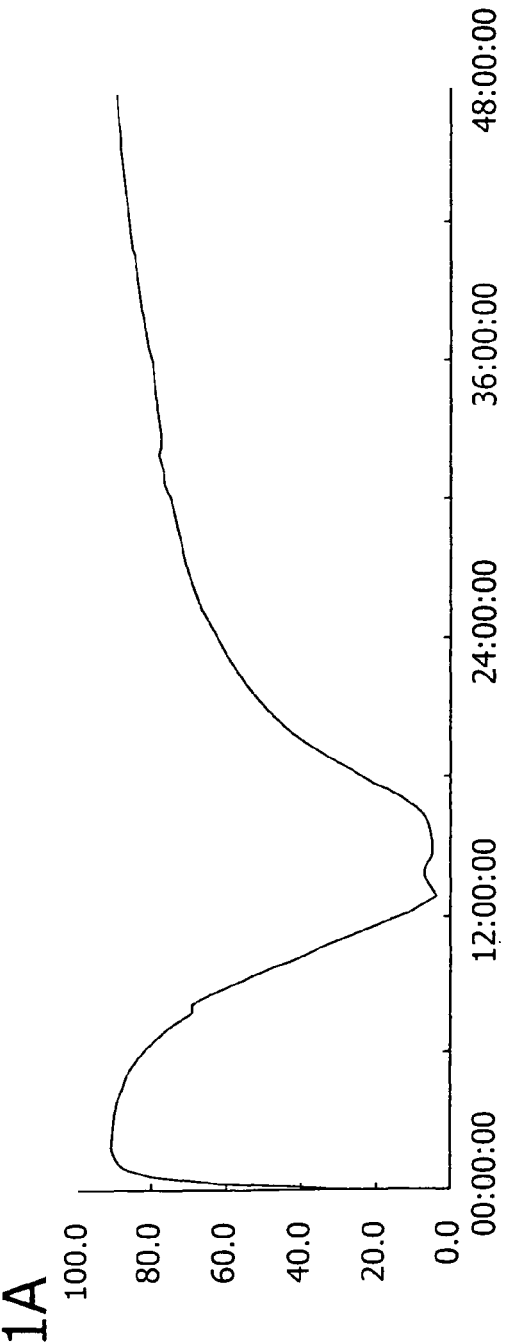
FIG. 1 shows a graph of percent saturation of dissolved oxygen (A) and pH (B) versus time of the sporulation medium during a successful sporulation when percent saturation of dissolved oxygen is not controlled.

1. Feed given to the birds
2. Water given to the birds
3A. Manure is harvested after birds begin shedding oocysts
3B. Manure is discarded prior to when birds shed oocysts 4. Water is added to a slurry tank containing the manure
5. The slurry is sieved
6. Solid waste from sieving is discarded
7. Filtrate collection transferred to and then separated by centrifugal-based separation
8. Liquid waste is discarded while moist solid is retained
9. Moist solid is transferred to mix tank
10. High fructose corn syrup is added to tank
11. Water is added (if needed) to adjust specific gravity
12. Suspension is transferred for separation
13. Solid wastes are discarded
14. Liquid phase is transferred to mix tank
15. Water is added to mix tank
16. Diluted suspension is transferred to and then centrifuged
17. Liquid waste is discarded
18. Solid transferred to blend vessel
19. Water is added to blend vessel
20. Diluted suspension is deposited in holding container then later transferred to sporulation vessel
21. An oxidizing agent is added to the sporulation medium
22. Sporulated oocysts transferred from sporulation vessel to separation device
23. Water is added to sporulated oocysts suspension
24. Waste water from separation is removed and discarded
25. Sporulated oocysts, now separated from sporulation medium, are transferred to sterile filtration unit
26. Addition of disinfecting agent
27. Addition of sterile water
28. Waste water and disinfecting agent are discarded
29. Transfer to holding vessel
30. Addition of buffer
31. Addition of bactericide
32. Transfer to blending vessel where buffer and post-challenge performance improvement composition are blended
33. Vialing
34. To kit or to market

DETAILED DESCRIPTION

The following detailed description is provided to aid those skilled in the art in practicing the present invention. Even so, this detailed description should not be construed to unduly limit the present invention as modifications and variations in the embodiments discussed herein can be made by those of ordinary skill in the art without departing from the spirit or scope of the present inventive discovery.

All publications, patents, patent applications, databases and other references cited in this application are herein incorporated by reference in their entirety as if each individual publication, patent, patent application, database or other reference were specifically and individually indicated to be incorporated by reference.

As used herein, the term "domestic water" refers to available (potable) tap water.

The present invention provides for the substantial elimination of added potassium dichromate in the production of vaccines used for the prevention of coccidiosis in animals, and in particularly poultry. More specifically, the composition of the invention is a novel vaccine ready for administration. The composition of the invention herein, in a preferred embodiment, is substantially free of alkali metal dichromates, soluble dichromates, dichromate ions, and potassium dichromate when the methods disclosed herein are practiced. Any alkali metal dichromates, soluble dichromates, dichromate ions, and potassium dichromate present in the compositions described herein or present in the compositions made by the methods described herein would be residual and, in a preferred embodiment, would not be present due to affirmative addition. In addition, the present invention provides methods for the sporulation of coccidial protozoa, the production of sterile preparations containing viable sporulated oocysts that are substantially free of potassium dichromate, and compositions and methods for storing sporulated oocysts.

Furthermore, the invention provides a method for the monitoring of the sporulation process that does not require microscopic examination of the oocysts. Furthermore, the invention provides for kits containing a composition used for the prevention of coccidiosis in animals, and in particularly poultry characterized as substantially free of potassium dichromate.

Oocysts used in the practice of the present invention can be obtained from a variety of sources. For example, oocysts can be obtained by the inoculation of host animals with coccidial protozoa of a single species or with a mixture of species. The coccidial protozoa used can be clonal in nature, that is derived from a single progenitor, or polyclonal. The oocysts of the present composition are derived from wild type oocysts. Inoculation can be by any means which will allow for the replication of the protozoa in the host animal. The most common route of inoculation is per os, but other suitable routes may be used. If administered per os, the protozoa are preferably at the sporulated oocyst stage. Administration can be by gavage or through the feed and/or water. Inoculation can also be accomplished by exposing host animals to environments contaminated with coccidial protozoa. Alternatively, oocysts can be obtained from animals with naturally occurring infections.

The present invention provides a method for the sporulation of oocysts comprising first orally inoculating host animals with *Eimeria* species. Manure from the innoculated animals is then collected from the inoculated host animals. Oocysts are separated from the manure using a combination of isolation techniques, including sieving, centrifugation and density flotation. The isolated oocysts are then sporulated under certain defined conditions controlling factors such as temperature, percent saturation of dissolved oxygen, pH, and agitation in a sporulation medium. The sporulated oocysts are then separated from the sporulation medium and disinfected. After, the sporulated oocysts have been separated from the sporulation medium and disinfected they are combined with a diluent or a diluent and a buffer to form a vaccine. A post-challenge performance improvement composition may also then be added. Such a composition ameliorates a decrease in post-challenge performance. The amelioration may be seen in factors such as bursal growth and appearance. For illustrative purposes only, a preferred method is described graphically in the form of a flow sheet in FIG. 5.

Furthermore, the invention provides for a method of monitoring sporulation without the need for microscopic observations. Microscopic observation requires sampling and technician labor. The elimination of microscopic observation provides a more efficient method for monitoring sporulation. The method of the invention for monitoring sporulation comprises monitoring oxygen consumption, as evidenced by a change in dissolved oxygen content, and monitoring pH. It has been discovered that sporulation results in an increase in oxygen consumption, as evidenced by a decrease in dissolved oxygen in a sporulation medium, and that sporulation results in an increase in pH. See FIGS. 1 and 2. Sporulation rates may be monitored by monitoring the volume and flow rate of an oxygen containing gas added to control percent saturation of dissolved oxygen and also may be monitored by monitoring the acid or base added needed to maintain a desired pH. Thus, the decrease in dissolved oxygen is a differential decrease sufficient to trigger the addition, by a controlled device, to supply more oxygen. In addition, the decrease in pH is also a differential decrease that is sufficient to trigger the addition of an acid or a base.

Methods of Isolation, Concentration, and Purification

In general, a number of different methods of preparing oocysts for sporulation are known in the art. Any one or combination of such methods may be used prior to sporulation. However, a preferred method is set out below. A number of well known processes are set forth to assist one skilled in the art to practice the invention in its different embodiments.

To begin, once host animals begin shedding the organism, the protozoa can be collected. Most commonly, protozoa are collected from the feces, but they can also be collected from intestinal contents and/or scrapings as well as contaminated bedding (see FIG. 5A, "Challenge Suite"). Once collected, the oocysts are preferably isolated from the extraneous fecal material as decreasing the fecal content in an oocyst suspension increases the number of oocysts that will sporulate (Smith and Ruff, *Poultry Sci.* 54:2083, 1975). As will be described below, a preferred method for isolating oocysts is by sieving (see FIG. 5A, step 5). However, several methods for isolating protozoa are known in the art and may be used in practicing the present invention. A summary of these isolation methods are summarized herein followed by a description of the preferred method. Several methods described herein process the collected manure to a point wherein sporulation may then begin. Others require further processing, such as further isolation or cleansing. This further processing may be accomplished by utilizing the methods and techniques described herein or a combination thereof.

A review of several methods for the isolation of oocysts can be found in Ryley et al. (*Parasitology* 73:311-326, 1976). In one method, described in U.S. Pat. No. 3,147,186, oocysts are only crudely isolated following the addition of the oxidizing agent potassium dichromate. In this method, the moist droppings of host animals are directly mixed with an aqueous solution containing between one and four percent potassium chromate, preferably 2.5% or, less preferably, water, so that a suspension of thin consistency is obtained. The method indicates that a concentration of at least about one to four percent potassium chromate solution is necessary to obtain adequate oocyst sporulation. Larger insoluble debris, such as feathers and partially digested or undigested feed, is removed. Removal can be done conventionally by filtering the suspension through a mesh screen. The suspension is then allowed to stand for about five minutes to allow heavier coarser particles of debris that passed through the screen to settle to the bottom of the holding container. The supernatant liquid containing the oocysts is then removed. The sporulated oocysts are viable for up to about 18 hours.

Another method for separating oocysts from droppings comprises flotation using solutions of sufficient specific gravity, typically having a specific gravity of about 1.2, so that oocysts float to the top of the suspension. Generally these solutions are made up of water to which a sugar (e.g. sucrose), $ZnSO_4$, or NaCl has been added to increase the specific gravity to the desired value. Useful solutions include solutions comprising 58% (w/v) sucrose, 37% (w/v) $ZnSO_4 \times 7H_2O$ and saturated NaCl solutions, which all have a specific gravity from about 1.09 to about 1.2. Other solutions which have a comparable specific gravity and are not harmful to the oocysts can also be used.

In the flotation method of isolation, a preliminary step of filtering diluted collected manure through, e.g., gauze, a sieve or cheesecloth to remove large particles of undesired fecal matter may be included. After mixing harvested oocysts with the flotation solution, the oocyst slurry may be centrifuged and the oocyst removed from the surface layer of the supernatant. The centrifugation step may be repeated several times to further purify the oocysts by resuspending the captured supernatant in a flotation medium having a specific gravity similar to that used in previous centrifugation steps and centrifuged again. This step may be repeated until the desired level of purity is reached.

Another method for isolation of oocysts available in the art comprises gradient centrifugation. The gradient used can be discontinuous or continuous. An example of a typical gradient for coccidial oocysts is 0-50% sucrose. In this method the material containing the oocysts is placed on top of the gradient and the oocyst containing material is then centrifuged along with the gradient. Following centrifugation, the layer containing the oocysts is recovered. The process may be repeated in order to increase the purity of the resulting oocyst preparation. As with flotation, this method is preferably preceded by filtration of the collected manure.

Additional methods of oocyst isolation include, the use of glass bead columns (Ryley et al., *Parasitology*, 73:311-326, 1976) and the bicarbonate ether method (Smith and Ruff, Poultry Sci. 54:2081-2086, 1975). In the glass column method, the aqueous suspension of fecal matter is added to a mixture of glass beads and a detergent, for example 5% Tween 80. The mixture is then applied to a column of glass beads and the oocysts are allowed to flow through while much of the undesired fecal matter is retained in the column. The effluent may then be concentrated by centrifugation.

In the bicarbonate ether method, the feces from infected chickens is strained, through cheese cloth for example, and the liquid fraction is captured while the solid fraction is discarded. The liquid fraction is then concentrated by centrifugation. The solid fraction is recovered and the supernatant is discarded. The recovered solid fraction is then resuspended in a solution of 1% sodium bicarbonate. To the resuspended solid fraction, now in suspension, is then added ether in a volume approximately equal to the volume of 1% solution of sodium bicarbonate. The mixture is then centrifuged. The debris plug and supernatant is discarded while the sediment is washed by resuspension in water. This suspension is then centrifuged and the supernatant discarded. The sediment is then recovered for use. (Smith and Ruff, *Poultry Sci.* 54:2081-2086, 1975).

The various methods for isolating, concentrating, and purifying oocysts describe above may be used in combination with one another or in combination with the preferred embodiments of the instant invention. Regardless of the methods used, the greater the isolation, concentration, and purification the greater percent sporulation during the sporulation suite (see FIG. 5, "Sporulation Suite"). Therefore, it has been discovered that the following methods of isolation, concentration, purification, sporulation, sterilization, and storage provide a novel and improved method for the production of sporulated oocysts.

One aspect of the method of the instant invention comprises collecting manure from host animals wherein said manure contains oocysts known to cause coccidiosis; diluting said manure in an aqueous medium to create a slurry; separating unwanted fecal matter from said slurry and collecting the aqueous fraction containing oocysts; subjecting said aqueous fraction to solid/liquid phase centrifugal-based separation and collecting the solid phase; combining a dense aqueous liquid with said collected solid phase wherein said dense liquid has a density greater than about 1.09 g/ml and wherein the oocysts are buoyant; subjecting the combination of said dense aqueous liquid and collected solid phase to centrifugation and collecting the dense liquid fraction containing oocysts, diluting said dense liquid fraction to a specific gravity wherein the oocysts are no longer buoyant; separating oocyst solids from said diluted liquid fraction by centrifugal-based separation and re-collecting the solid phase.

In another aspect the method for isolating oocysts comprises collecting manure from host animals wherein said manure contains oocysts known to cause coccidiosis; diluting said manure in an aqueous medium to create a slurry; separating unwanted fecal matter from said slurry and collecting the aqueous fraction containing oocysts; subjecting said aqueous fraction to solid/liquid phase centrifugal-based separation by means of a hydrocyclone.

In yet another aspect, the method for isolating oocysts comprises collecting manure from host animals wherein said manure contains oocysts known to cause coccidiosis; diluting said manure in an aqueous medium to create a slurry; separating unwanted fecal matter from said slurry and collecting the aqueous fraction containing oocysts; subjecting said aqueous fraction to solid/liquid phase centrifugal-based separation and collecting the solid phase; combining a dense aqueous liquid with said collected solid phase wherein said dense liquid has a density greater than about 1.09 g/ml and wherein the oocysts are buoyant; subjecting the combination of said dense aqueous liquid and collected solid phase to centrifugation and collecting the dense liquid fraction containing oocysts, diluting said dense liquid fraction to a specific gravity wherein the oocysts are no longer buoyant; separating oocyst solids from said liquid phase by means of a hydrocyclone and re-collecting the solid phase.

A further aspect of the methods provided herein describes a method for sporulating oocysts comprising introducing into an aqueous sporulation medium oocysts of at least one species of protozoa known to cause coccidiosis; incubating said oocysts in said aqueous sporulation medium; and introducing an oxidizing agent into said medium at a rate sufficient to maintaining the dissolved oxygen content of the medium at at least 30% of saturation; said medium containing less than about 0.8% by weight alkali metal dichromate during incubation of said oocysts.

Another aspect of the methods provided herein describes a method for sporulating oocysts comprising introducing into an aqueous sporulation medium oocysts of at least one species of protozoa known to cause coccidiosis; incubating said oocysts in said aqueous sporulation medium; and introducing an oxidizing agent into said medium at a rate sufficient to maintaining the dissolved oxygen content of the medium at between about 30% and about 80% of saturation; said medium containing less than about 0.8% by weight alkali metal dichromate during incubation of said oocysts.

In another aspect of the methods provided herein is described a method for separating sporulated oocysts from a sporulation medium; sterilizing sporulated sporocysts by contacting said sporulated oocysts with a chemical disinfectant; and storing said sporulated oocysts in a sterile diluent, wherein said diluent contains less than about 0.8% by weight alkali metal dichromate.

In another aspect of the methods described herein is described a method for inducing sporulation of oocysts comprising introducing into an aqueous sporulation medium oocysts of at least one species of protozoa known to cause coccidiosis; incubating said oocysts in said aqueous sporulation medium; and introducing an oxidizing agent having a standard reduction potential of at least about 0.5 V at a rate sufficient to maintain the oxidation potential of said medium equivalent to the oxidation potential of a medium containing dissolved molecular oxygen in concentration of at least 30% of saturation; said medium containing less than about 0.8% by weight alkali metal dichromate during incubation of said oocysts.

In yet another aspect of the instant invention, there is described a method for monitoring sporulation comprising incubating viable oocysts in an aqueous sporulation medium; and during incubation, monitoring said medium to detect a change in at least one of the following parameters: (i) dissolved oxygen content; (ii) pH; (iii) rate of introduction of oxidizing agent into said medium; (iv) flow rate of acid or base into said medium.

In another aspect of the instant invention, there is provided a composition for the storage of sporulated oocysts comprising 0.5×PBS; and about 30 μg/ml gentamicin, wherein said composition is characterized as substantially free of alkali metal dichromate, and further characterized in that oocysts in contact with said composition decrease in viability no more than about 20% over a period of at least about 26 weeks at about 5° C.

In a further aspect of the instant invention, a method of storing sporulated oocysts is provided that comprises contacting sporulated oocysts with the storage composition described above.

In yet but another aspect, the instant invention provides for a kit comprising a composition containing, sterile, viable, sporulated oocysts of at least one species of protozoa known to cause coccidiosis, said composition containing 0.8% by weight of alkali metal dichromate; and instructions for administration of said composition to an animal.

The preferred methods for isolation, concentration, flotation, sporulation, monitoring, separation, and sterilization, are now described.

Oocyst Isolation

The initial isolation of oocysts from the gross fecal matter is desired to remove large debris and fecal matter from a manure slurry. Thus, the step begins with a manure slurry highly contaminated with gross particles and results in a aqueous manure slurry substantially free of gross particles. Although isolation may be achieved by one of the above methods known in the art, isolation in the present invention is accomplished by filtering. In a preferred embodiment, the filtration is by sieving.

In one embodiment, the initial isolation is achieved by collecting manure from host animals, mixing the manure with domestic water, and then sieving. In one embodiment, the process begins with collected manure, e.g., a batch of several hundred pounds, made into a aqueous slurry and processed to concentrate oocysts as a suspension in a relatively small volume of aqueous medium, e.g., a several hundred pound batch of manure may ultimately yield about two liters of oocysts in an aqueous suspension (see FIG. 5A, "Challenge Suite", steps 1-3B). In this embodiment of the invention, sieving is by means of shaker screens, such as multiple tier shaker screens.

In one embodiment, the manure from the chickens is placed into a mixing vessel either by hand, e.g. using a shovel, or by using a mechanical dumper. Domestic water is added at a minimum ratio of about 1 gallon per each six birds' manure (see FIG. 5A, steps 3A and 4). Alternatively, the collected manure is mixed with domestic water at a ratio from about 2 to about 6 pounds of collected manure per gallon of water. As manure quantity is approximate and dilution is realized by using an approximation of the manure quantity, the dilution range is therefore also approximate. The slurry is then mixed until homogeneous. Feathers and other large, floating debris may be skimmed off the surface with an appropriate tool, e.g., a wire screen.

Typically, a sample is taken from the homogenous slurry prior to the screening/isolation process to assess oocyst count. Such count is done, for example, by microscopic visual examination. The homogenous slurry is then pumped onto a two-tier vibratory shaker screen. The top screen can be from about 150-mesh to about 350-mesh while the bottom screen can be from about 25-mesh to about 75-mesh. In a preferred embodiment, the top deck is equipped with a 50-mesh screen, the "top screen," while the lower deck has a 250-mesh screen, the "bottom screen." Larger unwanted fecal solids are separated at the top deck 50-mesh screen while smaller unwanted fecal solids are separated from the slurry at the lower deck, 250 mesh screen. A preferred flow rate onto the top deck screen is approximately 1 liter per minute per 12.1 $m^2$. The optimal flow rate of the pumping varies with the solids content and the condition of the screen. Larger or smaller screens may be used depending on the scale of the operation.

The oocysts are contained in the liquid fraction of the screening/isolation process. If the solid material coming off either the top or the bottom screen is too wet, recovery is unacceptably low as isolation of the oocysts from the homogenous slurry is not occurring. On the other hand, if too much water is removed, the solids stick to the screen and do not clear themselves. Eventually, depending on solid matter content and flow rates, so much material can accumulate that it may be necessary to remove it. The screens can be lubricated with water, allowing the screens to clear themselves. The liquid fraction is collected and sent on for concentration while the solid fraction is discarded (see FIG. 5A, step 6).

The solids coming off both of the screens are checked for oocysts and then discarded. If less than 5% of the oocysts loaded onto the screens are found in the solids, then the solids are discarded. If more than 5% of the oocysts loaded onto the screens are found in the solids, the solids are resuspended in an aqueous slurry and recycled through the sieves. The liquid that passes through both screens, the filtrate, is the fraction that contains the oocysts. This filtrate is collected into a receiving vessel (see FIG. 5A, step 7) and then sent to a centrifuge, preferably a bottle centrifuge or, alternatively, a decanter centrifuge.

In this non-limiting embodiment, the sieving method can be carried out in temperatures ranging from a low temperature that substantially avoids freezing to a high temperature that substantially avoids damage to the oocysts, preferably at room temperature. Lower temperatures, about 4° C., are preferred when sieving procedures take over more than three hours to protect the viability of the oocysts. In addition, the sieving process can be carried out at any rate throughput allows as long as the screens do not accumulate excessive solid matter and at a rate rapid enough to prevent the manure from drying. As with other steps of the invention, equipment should be clean prior to use.

Concentrating the Filtrate

The liquid oocyst-containing fraction recovered, from any one of the preceding methods used to initially isolate oocysts, is then concentrated. Isolated oocysts are concentrated to increase sporulation rates and output. Concentration is realized by various means, including substantial separation from the aqueous slurry, centrifugal-based separation or centrifugal-based separation followed by filtration. Concentrating the oocysts is accomplished by utilizing one or more of such techniques in combination with others. As used herein, centrifugal-based separation includes processing in either a mechanical rotated centrifugation or a static hydrocyclone. In one embodiment, centrifugation is by decanter centrifugation. Other methods are also known in the art and disclosed herein. Centrifuge scale and capacity varies by batch size. For larger batch size, the use of a decanter centrifugation or use of a hydrocyclone would be preferred. For smaller batch size, bottle centrifugation is preferred.

In one method, a combination of first sieving the collected manure, as described in the preferred sieving process above, is followed by continuous centrifugation and then filtration. In this method preliminary purification is achieved by sieving a homogenous slurry of collected manure through sieves having progressively smaller openings. Further purification is achieved by continuous centrifugation of the liquid fraction captured from the sieving process using a suspension wherein the suspension has a specific gravity preferably between about 1.01 to about 1.08 g/l. As a further purification step, the solid material recovered from the centrifugation, which contains the oocysts, is re-slurried and filtered using a membrane of a pore size that retains the oocysts, but allows the passage of smaller material, including bacteria. This process eliminates the flotation step, as described below.

Figure 5A:
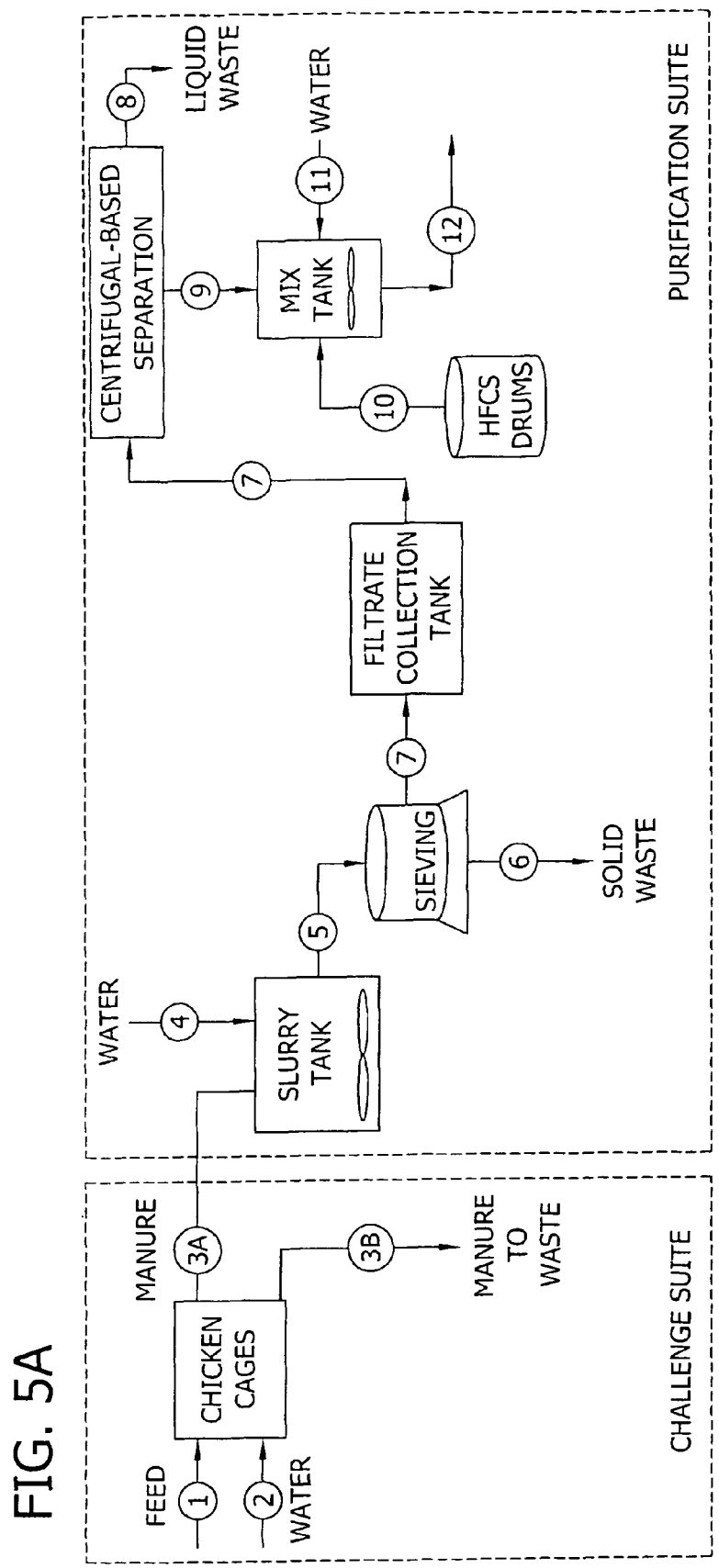
FIG. 5 shows a flow diagram of the process used to produce oral coccidiosis vaccine. The flow chart is divided into four suites: (1) Challenge Suite; (2) Purification Suite; (3) Sporulation Suite; and (4) Storage Suite. Steps 1 through 34 are described for illustrative purposes as follows.

In an example of a further alternative procedure, the material passing through the sieves can be further purified by being collected and pumped into a continuous flow centrifuge maintained at about 40-50° F., discarding the centrate, and collecting the solid material containing the oocysts (such as seen in FIG. 5A, step 8).

In a preferred embodiment, the filtrate recovered from the multi-screen screening/isolation process described above is then concentrated using a centrifuge. In one embodiment, the filtrate recovered from the multi-screen screening process described above is then concentrated using a bottle centrifuge. In a preferred embodiment, the filtrate recovered from the isolation/screening process is then concentrated using a bottle centrifuge wherein the filtrate is poured into centrifuge bottles and centrifuged at 1200×g for about ten minutes. The solid fraction formed contains the oocysts. The supernatant is then poured off (see FIG. 5A, step 8) and, if the solid fraction volume allows, more filtrate is poured on top of the solid fraction. At some point, the solid fraction will need to be removed as more oocysts collect. The oocysts may be loosened or removed with a spoon or spatula. Residual material that is still in contact with the centrifuge bottles may be rinsed out using a minimal amount of domestic water. The oocysts then require suspension in sufficient water to bring the solids content to less than about 70% of the total volume of the suspension, preferably less than about 60% of the total volume, and most preferably less than about 50% of the total volume, and should bring the suspension to substantial homogeneity. During this suspension process mixing of the aqueous suspension should be sufficient to keep the solids suspended, but the mixing should not create foaming. This suspension may then be further processed by the flotation step, described herein below.

In an alternative preferred embodiment, the filtrate from the multi-screen screening process described above, is pumped into a decanter solid bowl continuous centrifuge at a rate of approximately 3 to 4 liters/min. The decanter is set with a bowl speed of at least about 4000 RPM and a conveyor speed of at least about 2500 RPM and no more than about 3600 RPM. A receiving vessel is placed to catch the solids as they are expelled from the solid discharge of the decanter centrifuge. Under these conditions, solids are discharged as a runny paste. The liquid coming out of the liquid discharge of the decanter centrifuge is checked for oocysts and discarded if the liquid contains less than about 2% of oocysts initially loaded into the decanter centrifuge. If the liquid waste contains greater than or about 2% of oocysts initially loaded into the decanter centrifuge, the liquid should be re-mixed with the solids and run again until the liquid waste contains less than 2% of oocysts initially loaded into the decanter centrifuge.

In a preferred embodiment, once all the filtrate is pumped into the decanter centrifuge, the centrifuge is allowed to run for a period of time sufficient to move the residual solids out of the decanter. In one embodiment, this period of time is more than about two but less than about five minutes. Use of various sized centrifuges will vary the period of time and may be adjusted by one skilled in the art. In a preferred embodiment, the speed of the bowl is then lowered to about 1000 RPM and the speed of the conveyor lowered to about 500 RPM. The length of time and the bowl speed also varies according to batch size and can be properly adjusted by one skilled in the art. Domestic water may be sprayed into the access port to wash solids off the inner surfaces of the body of the decanter. The solids are then moved to an appropriate volume centrifuge bottle for the flotation step, described below. It is important to clean the equipment after each run and may be accomplished by the use domestic water sprayed from a hose in order to obtain greater yield.

In yet another embodiment, a hydrocyclone is used to concentrate the filtrate obtained from sieving. It has been discovered that a hydrocyclone, traditionally used in the petrochemical and environmental science fields is useful for concentrating oocysts. Hydrocyclones use the principle of centrifugal separation to remove or classify solid particles from a fluid, based on size, shape, and density. The use of a hydrocyclone, not known to be used for living organisms, was previously believed to fatally damage the oocysts due to intense sheer forces. The instant invention provides a method of utilizing a hydrocyclone to concentrate oocysts. In one embodiment, the hydrocyclone used is a Dorr-Oliver DOXIE Type 5 Hydrocyclone (available from GL&V/Dorr-Oliver, Millford, Conn.).

In a preferred embodiment involving the use of a hydrocyclone, a reservoir containing the filtrate obtained from sieving is connected to a pump. The pump delivers the filtrate to the hydrocyclone at a pressure of between about 120 psi and about 130 psi and at a feed rate from about 1 to about 3 gallons per minute, preferably about 2 gallons per minute. A preferred hydrocyclone has one inlet and two outlets. Each outlet is equipped with a needle valve to regulate the flow through each orifice. By regulating the flow between the upper and lower outlets, it is possible to remove a significant amount of liquid through the upper outlet while retaining most of the denser materials, including the oocysts, in a concentrated suspension through the lower outlet. In a preferred embodiment, a 2 to 1 ratio between the flow of material collected from upper outlet and lower outlet. Such 2 to 1 ration produces an optimal recovery of oocysts. The recovered concentrated material, that is, the material collected from the lower outlet, may be recycled through the hydrocyclone for greater concentration if further volume reduction is desired. The suspension collected from the upper outlet is discarded. For large volumes of filtrate, it may be advantageous to operate hydrocyclones in parallel or utilize larger scale equipment to increase throughput.

Floating the Oocysts

To further isolate the oocysts collected from the concentration methods described above from unwanted solids, such as fecal matter, grit, etc., the oocysts are floated to the top of a solution using density variations. In an alternative embodiment, the oocysts may be added to a sucrose solution and centrifuged. In yet another alternative embodiment, the oocysts may be added to a sucrose solution and then filtered. In a preferred embodiment, the oocysts are floated to the top of a solution comprising domestic water and high fructose corn syrup and having sufficient density to allow the oocysts to float to the top of the suspension while the heavier unwanted solids migrate to the bottom of a holding vessel or vessels. In a preferred embodiment, the oocysts are isolated from the dense solutions using centrifugation. The oocysts are then recovered from the liquid phase in this step of the invention.

Figure 5B:
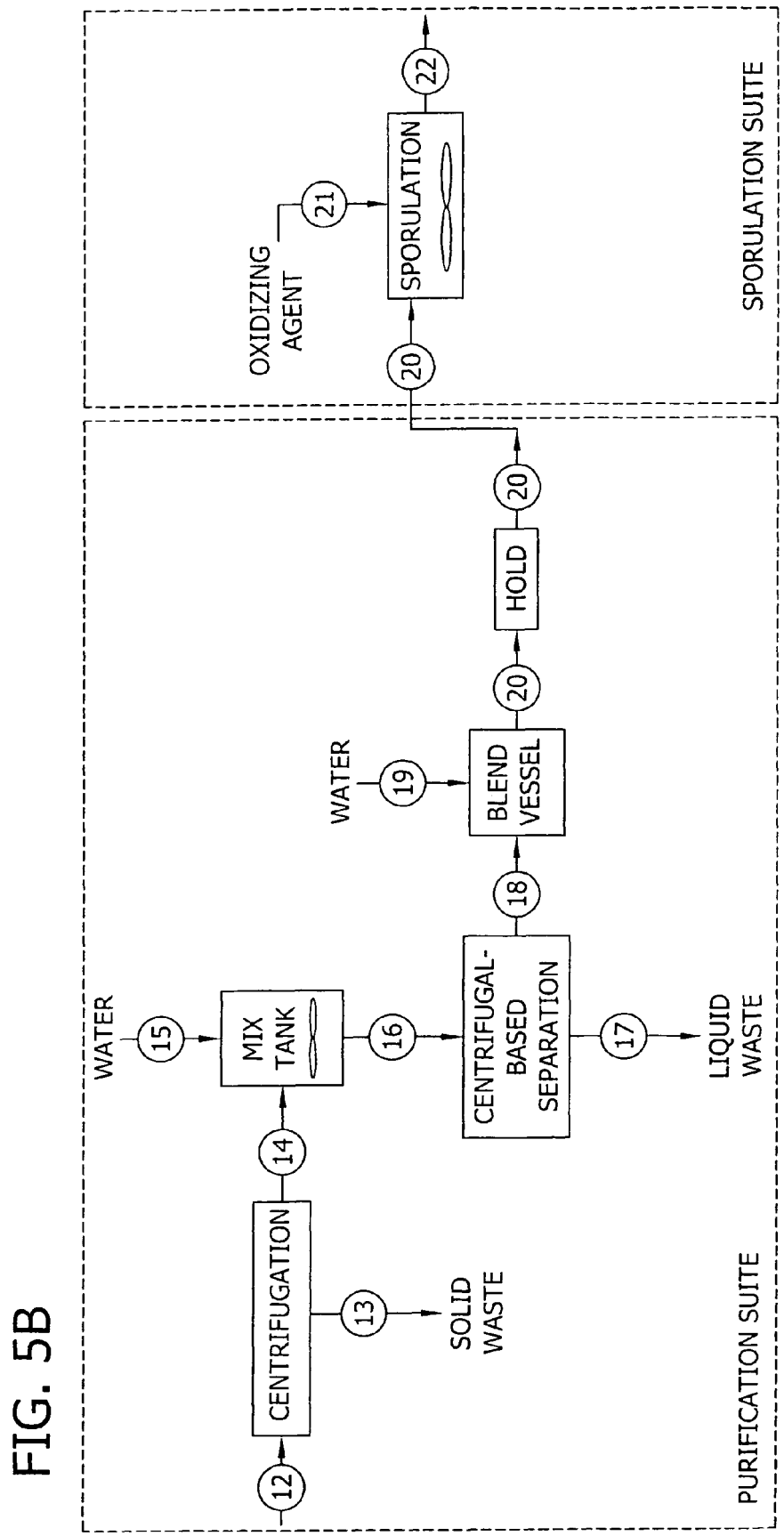

In one embodiment, the solid material containing the oocysts recovered from centrifugation is transferred to a mix tank and to a concentrated sucrose or high fructose corn syrup (HFCS) of volume equal to that of the oocysts is added. A water of a volume equal to that of the oocyst/HFCS solution is added for a total final volume of about four times the volume of the initial solids (FIG. 5A, steps 9-11). The final mixture is then pumped into a continuous centrifuge at a rate to allow the oocysts to remain in the centrate and solids are discarded (FIG. 5B, steps 12-13). If desired, further concentration of the oocysts and dilution of and substantial removal of the residual sugar solution is accomplished by addition of domestic water and continuous flow centrifugation at a feed rate which allows separation of the phase containing the oocysts from the sugar solution phase. In an alternative embodiment, the oocysts/HFCS solution can be centrifuged in a bottle centrifuge. In this case, the supernatant is discarded and the oocysts in the resulting solid fraction are resuspended in water. In yet another alternative embodiment, the residual sugar can be removed by filtration using filters with a pore size which excludes the oocysts. When filtration is used, tangential flow is preferred. Tangential flow filtration is characterized in that an influent stream is separated into two effluent streams, known as permeate and retentate. The permeate is that fraction which has passed through the "semipermeable" membrane (or filter pad). The retentate is that stream which has been enriched with the solutes of suspended solids which have not passed through the membrane (or filter pads). Water can be continually added to the retentate vessel at the same rate at which the sucrose-rich permeate is leaving in order to avoid over concentration of the solids. Once sufficiently filtered, the retentate, containing the isolated oocysts, can then be stored in any suitable medium and temperature until sporulation. In one embodiment, the isolated oocysts are placed in sterile water and stored at about 2-8° C.

In a preferred embodiment, the decanter centrifuge method of concentration, described above, is used to concentration the filtrate retained from sieving and the volume of solids obtained from a decanter centrifuge is measured by volumetric measurement. Such measurement may be taken by centrifuging about 50 ml of the concentrated filtrate for about 10 minutes at 1,500×g ($r_{average}$) in a centrifuge with 50 ml conical tube adapters. Any centrifuge that produces the preferred forces on the filtrate may be used. The percent solids is calculated by multiplying the volume of the solid by 2. Other well known methods may also be used to calculate solids and can be determined by one skilled in the art. The solids content is then adjusted to less than 60% solids, with domestic water, if necessary. More preferably, the percent solids is brought to below about 50% solids by the addition of domestic water, and most preferably the percent solids is brought to below about 40% solids by the addition of domestic water.

Then a HFCS solution, in a percent volume from about 30% to about 40% of the solid collected from the concentration/centrifugation step, is added. This typically brings the density of the liquid phase up to the point where the oocysts float. The density of the liquid is brought up to at least 1.09 g/ml and can be brought up to an amount higher than 1.09 g/ml. The density of the liquid is preferably between 1.09 g/ml and about 1.20 g/ml, more preferably to be between 1.09 g/ml and about 1.14 g/ml, and most preferably to be between about 1.09 g/ml and about 1.10 g/ml. If the density of the liquid is less than 1.09 g/ml, remix the oocyst-containing liquid with additional HFCS solution until the density is at least 1.09 g/ml. This dense liquid is then poured into vessels proper for centrifuging, the vessels are balanced with respect one another in their placement in the centrifuge, and then centrifuged.

In a preferred embodiment, the dense liquid is centrifuged at a temperature from about 4° C. to about 10° C. The density of the liquid phase is then measured following the first centrifuge run using methods well known in the art. If the density of the liquid is less than 1.09 g/ml, one should re-mix the liquid phase and the solid phase and add more high fructose corn syrup solution to obtain a density of 1.09 g/ml or greater. These steps can be repeated if necessary in order to obtain the highest yield of oocysts.

In a preferred embodiment, to the resuspended oocysts from the concentration step described above, is added a volume of HFCS equal to about 30% to about 40% of the volume of the solid fraction. HFCS is added until the density of the liquid phase is brought up to the point where the oocysts float, a density of about 1.09 to about 1.14 g/ml. The entire suspension of oocysts in the HFCS/domestic water suspension is then separated from the HFCS (see FIG. 5B, step 12).

In one embodiment, the HFCS/domestic water suspension is poured into centrifuge bottles, balanced with respect one another in their placement in the centrifuge, and centrifuged for about 15 minutes at 3750×g ($r_{max}$) and at a temperature from about 4° C. to about 10° C. The buoyant oocysts float to the top of the suspension while heavier unwanted solids settle to the bottom of the bottles. The solids contained in the supernatant should contain no more than about 40% solids. If the percent solids found in the supernatant, measured according to the volumetric method described above, is higher than about 40%, then the density is too high and the entire suspension needs to be diluted with domestic water and re-centrifuged.

In using the bottle centrifuge method of centrifuging, a large number of the oocysts will remain in contact with the bottle near the top of the supernatant. This oocyst-containing material may be freed and returned to the supernatant, for e.g., by swirling the bottles or by using a tool, such as a spatula. This will not disturb the solid phase. The bottles may be swirled by hand at room temperature to remove the crust of oocysts on the bottle. In larger batch sizes the vessel used for centrifuging can be cleaned by those methods familiar to one skilled in the art in order to clean the vessel and recover a higher percentage of oocysts.

The supernatant is then poured off into a vessel. If using the bottle centrifuge, rotating the bottles while pouring helps rinse the oocysts off the sides. The solid fraction can then be discarded. The same centrifuge bottles can then be refilled and the process repeated until all of the dense liquid has been centrifuged. The oocysts are now ready to go to the second concentration step which removes residual sucrose.

Concentrating the Oocysts after Flotation

The liquid fraction from the floatation step described above is then diluted with domestic water and the separated from the HFCS. In this process, the oocysts are concentrated prior to the sporulation step. The concentrated oocysts are then diluted yet again and held prior to sporulation.

In one embodiment the liquid phase recovered from the flotation centrifugation step is first diluted with domestic water till the oocysts sink and then centrifuged to capture the oocysts in the solid phase (FIG. 5B, steps 15-18) to remove a substantial amount of HFCS. In another embodiment, the liquid phase recovered from the flotation centrifugation step is first diluted with domestic water till the oocysts sink and the suspension is processed with a hydrocyclone. In using the hydrocyclone, the upper fraction is recovered. Subsequent separation of the HFCS, the concentrated oocyst containing suspension is again diluted with domestic water and transferred to a holding vessel prior to sporulation (FIG. 5B, steps 19-20).

In a preferred embodiment, the volume of the liquid fraction recovered from the flotation step is measured and a sample is taken to assess oocyst count. Sufficient domestic water is added to lower the density of the supernatant to less than about 1.04 g/ml. This allows the oocysts to sink. The density is measured following the addition of the domestic water using techniques well know in the arts. If the density is not less than about 1.04 g/ml and/or the oocysts have not sunk, additional domestic water is added until such density is reached and/or the oocysts sink. The oocyst suspension is then poured into centrifuge bottles and centrifuged for about 10 minutes at 1200×g from about 4° C. to about 10° C. The supernatant is tested for oocyst presence by counting using a microscope and hemocytometer and the supernatant is discarded if an acceptable amount of oocysts are counted in the supernatant. An acceptable amount of oocysts in the supernatant is from about 1% to about 5%, preferably about 2%, of the total oocysts loaded at the beginning of flotation step. More of the mixture from the flotation step is then poured on top of the solid fraction generated by centrifugation. While not necessarily being resuspended, the solid fraction is loosened somewhat, particularly by inverting the bottle a few times. The resuspended solid fraction suspension is then centrifuged as before, for about 10 minutes at 1200×g from about 4° C. to about 10° C., and the process is repeated until the flotation step mixture has all been centrifuged.

When using the bottle centrifugation method, at this point, there should be several bottles, each with a solid fraction in the bottom. Note, however, with larger batch size the vessel or vessels vary with equipment that is of appropriate volume and recovery methods may be determined by one skilled in the art. The solid fractions in the centrifugation vessels are then resuspended by shaking them with a minimal amount of domestic water. The solid fractions are rinsed into one or two of the bottles and the bottles filled and balanced with water if necessary. These bottles are centrifuged one last time as before, for about 10 minutes at 1200×g from about 4° C. to about 10° C. The supernatant is then discarded. Any loose solid fractions that comes out with the supernatant can be ignored. The solid fraction is then resuspended in a minimal amount of domestic water and stored in a single bottle from about 2° C. to about 5° C. pending sporulation while freezing should be avoided.

In an alternative embodiment, the HFCS in the liquid phase recovered from the flotation step can be remove by filtration using filters with a pore size which excludes the oocysts. When filtration is used, tangential flow is preferred. Tangential flow filtration (TFF) is characterized in that an influent stream is separated into two effluent streams, known as permeate and retentate. The permeate is that fraction which has passed through the "semi-permeable" membrane (or filter pad). The retentate is that stream which has been enriched with the suspended solids which have not passed through the membrane (or filter pads). Once sufficiently filtered, the retentate, containing the isolated oocysts, can then be stored in any suitable medium and temperature until sporulation. In one embodiment, the isolated oocysts are placed in sterile water and stored at about 2-8° C. Note that the tangential flow filtration is an alternative embodiment to concentrating the oocysts after flotation and TFF at this step should not be confused with TFF used during sterilization.

In an alternative embodiment, the volume of the liquid fraction recovered from the flotation step is measured and a sample is taken to assess oocyst count. Sufficient domestic water is added to lower the density of the supernatant to less than about 1.04 g/ml. This allows the oocysts to sink. The density is measured following the addition of the domestic water using techniques well know in the arts. If the density is not less than about 1.04 g/ml and/or the oocysts have not sunk, additional domestic water is added until such density is reached and/or the oocysts sink. The oocysts suspension is then processed through a hydrocyclone at a flow rate of about 2 gallons per minute and at a pressure between about 120 psig and about 130 psig.

Batch size and scale will lead one skilled in the art to utilize various centrifugation processes based on batch size while one skilled in the art will also adjust the correct centrifugation speeds based on the batch size.

Sporulation

Sporulation is performed to transform the cleaned and concentrated oocysts into their next life form, the sporulated oocyst (see FIG. 5B, "Sporulation Suite"). Sporulation may be performed in any suitable container, however, a fermentation vessel is preferred in order to best control temperature, dissolved oxygen, pH, and mixing in addition to monitoring these parameters of the sporulation medium. The capacity of the sporulation vessel varies with batch size and can be adequately selected by one skilled in the art. A preferred fermentor is the New Brunswick BioFlow 3000 (available from New Brunswick Scientific Company, Edison, N.J.).

Sporulation is achieved by subjecting the oocysts to an oxidative challenge. In this step, the oocysts are contacted with an oxidizing agent which is effective to promote sporulation but does not result in the death of the oocysts. As described below, the oxidizing agent comprises a principal oxidant other than a source of dichromate. Preferably, the sporulation medium is substantially devoid of potassium dichromate, an alkali metal dichromate, dichromate ions or other dichromate salt. In a preferred embodiment, the sporulation medium contains less than about 0.8% by weight of alkali metal dichromate, or less than about 0.6% by weight of alkali metal dichromate, or less than about 0.4% by weight of alkali metal dichromate, or less than 0.2% by weight of alkali metal dichromate, more preferably 0.1% by weight of alkali metal dichromate, and most preferably the sporulation medium is substantially free of an alkali metal dichromate. In another preferred embodiment, the sporulation medium contains less than about 3.0% by weight of dichromate ions. In yet another preferred embodiment, the sporulation medium contains less than about 1.5% by weight hexavalent chromium.

In one embodiment of the invention, oocysts concentrated by the methods and processes of the instant invention and described above are collected over a time period sufficient to create a batch size suitable for a fermentation vessel of desired volume. The collected concentrated oocysts are then deposited in to a sporulation vessel, an oxidizing agent is added and sporulation is allowed to occur (see FIG. 5B, step 21). Domestic cold water is used to rinse the container or containers holding the oocysts prior to their contact with the fermentation vessel. The sporulated oocysts and the rinse is then transferred to a separation device (FIG. 5B, step 22). The instant invention also provides for sporulation by depositing concentrated oocysts in a fermentation vessel, subjecting the oocysts to an oxidative challenge by contacting the oocysts with an oxidizing agent, such as oxygen or sodium hypochlorite, in an aqueous medium, wherein the percent saturation of dissolved oxygen in the medium is maintained at preferred levels, pH is controlled between preferred levels by the alternative addition of an acid or a base, the suspension is mixed to near homogeneity, and temperature is between preferred temperatures over a preferred period of time. In a further aspect of the instant invention an anti-foaming agent is added during the sporulation process. Preferably solids do not exceed more than about 50%. Preferably solids are less than about 35%. More preferably still, solids are less than about 25%. Sufficient domestic water is added to the sporulation vessel to achieve this ratio between solid and liquid phase. The liquid phase in the fermentation vessel is termed the sporulation medium.

In a preferred embodiment the oxidizing agent used is oxygen. Oxygen may be added in the form of air or as pure oxygen.

In an alternative embodiment, sufficient 5.25% sodium hypochlorite is added to the fermentor to achieve the following initial concentrations upon dilution of active chlorine concentrations for the individual subspecies. The values are approximate and indicate preferred maximum concentrations that do not inhibit sporulation:

TABLE 1

| Spp. of Eimeria | weight % |
|---|---|
| *E. Acervulina* | 0.01 |
| *E. Maxima* | 0.05 |
| *E. Tenella* | 0.05 |

During sporulation, the percent saturation of dissolved oxygen content in the aqueous medium is maintained at at least 30% of saturation, preferably at at least 40% of saturation, and more preferably at least 50% of saturation. Percent saturation of dissolve oxygen is controlled, by supplying air or molecular oxygen, to achieve consistent and higher yields of sporulated oocysts.

In a preferred embodiment of the invention, percent saturation of dissolved oxygen is maintained by bubbling air through the mixture at a rate sufficient to meet the above ranges. Pure oxygen may also be bubbled through the mixture to maintain the requisite percent dissolved oxygen. Care should be taken so that the flow of oxygen is not so rapid as to cause foaming. If desired, an anti-foaming agent may be added, such as Antifoam A (available from Sigma-Aldrich, St. Louis, Mo.). Oxygen is added by any means practicable. Oxygen may be added by adding both air when lesser flow rates are needed. e.g., when oxygen consumption is relatively low to peak sporulation, to maintained the preferred percent dissolved oxygen saturation while molecular oxygen may be added when the need is greater, e.g., when oxygen consumption is greatest. Oxygen is preferably added at a flow rate of from about 0.1 to about 2.0 liters of gas per liter of material and more preferably from about 0.3 to about 0.5 liters of gas per liter of material. The flow rate may be kept constant despite a greater need to maintain preferred percent saturation of dissolved oxygen as the gas added may consist of air when less oxygen is needed and may consist of molecular oxygen when more oxygen is needed. The preferred fermentor automatically converts from the addition of air to molecular oxygen as needed while controlling a nearly constant flow rate.

The pH level is preferably maintained from about 7.0 to about 7.7, more preferably from 7.2 to about 7.5, and more preferably still the pH is maintained about 7.4. The pH level of the sporulation medium is controlled by adding an acid or a base. In a preferred embodiment, either sodium hydroxide (5N) or sulfuric acid (5N) is alternatively added to the sporulation medium as needed to maintain the pH near 7.4. When using a fermentation vessel, the acid and/or the base may be added by using a fermentation vessel's automatically controlled peristaltic pumps on the fermentor.

The temperature of the sporulation medium is controlled throughout sporulation. Oocysts are placed in a sporulation vessel at a temperature from a temperature that substantially avoids freezing to about 43° C.; preferably between about 15° C. to about 38° C.; and more preferably between about 20° C. to 30° C. and more preferably still at about 28° C.±1° C. It will be apparent to those of ordinary skill in the art that the rate of sporulation is temperature dependent, so that the time required for sporulation will generally be less at higher temperatures.

Throughout the sporulation process, the sporulation medium is mixed. Any suitable method of mixing can be used to mix the sporulation medium to about a homogenous state. The exact method of mixing varies depending on the container used. For example, when bottles or flasks are used, mixing can be achieved by the use of shakers, or magnetic or mechanical stirrers. When vats or fermentors are used, a mechanical stirrer, such as a paddle stirrer is preferred.

Although sporulation is substantially complete within 12 to 18 hours, removal of the sporulated oocysts prior to about 72 hours decreases viability. Therefore, sporulated oocysts are preferably kept under the above sporulation conditions for a preferred time period to provide a more stable population of sporulated oocysts. The oocysts are preferably maintained in the above conditions for approximately 72 to 120 hours, more preferably for 72 to 110 hours, and more preferably still for 72 to 96 hours, to allow sporulation to occur.

Sporulation start point, end point and rate may be monitored by monitoring: (1) the rate at which oxygen must be added to the sporulation medium to control percent saturated dissolved oxygen; and/or (2) by monitoring the amount of acid or based required to be added to control the pH of the sporulation medium. It has been discovered that sporulation results in an increase in oxygen consumption, as evidenced by a decrease in dissolved oxygen in the sporulation medium, and an increase in pH, that is, if percent saturation of dissolved oxygen and pH are not controlled. When no additional oxygen is added to the sporulation medium, sporulation is indicated by a drop in dissolved oxygen to less than 60% of saturation, more preferably less than 40%, and more preferably still less than 20%. The change in dissolved oxygen can also be measure in terms of percent change. Thus, sporulation can also be indicated by a decrease of at least 10% (i.e., from 50% to 40%), preferably at least 20%, more preferably at least 30%, and more preferably still at least 40% in dissolved oxygen content as expressed in percent of saturation (see FIG. 1A). When pH is not controlled by the alternative addition of an acid or a base, increase in pH of at least about 0.25 pH units, more preferably at least about 0.5 pH units, is indicative that sporulation is occurring (see FIG. 2).

The change in dissolved oxygen and pH do not occur independently. An increase in the oxygen consumption indicates the start point of sporulation. Note, however, that background oxygen consumption will be seen as the sporulation medium is not sterile at this point and so various bacteria will be consuming oxygen as well as the oocysts. However, the increase in oxygen consumption will be significant over the background oxygen consumption so that the sporulation start point, end point, and rate, including peak, are readily ascertainable. A decrease in oxygen consumption indicates a drop in sporulation rate. Once oxygen consumption becomes low and consistent, sporulation is substantially complete, usually after about 18 hours. However, as mentioned above, the sporulated oocysts should be maintained under the sporulation conditions for at least an additional 36 to 48 hours to increase yield. Monitoring of sporulation will assist the practitioner in reaching higher yields of viable sporulated oocysts. Optionally, sporulation can be confirmed by microscopic examination of the oocysts. However, the method of present invention obviates the need for sampling and microscopic examination.

Sterilization

Figure 5C:
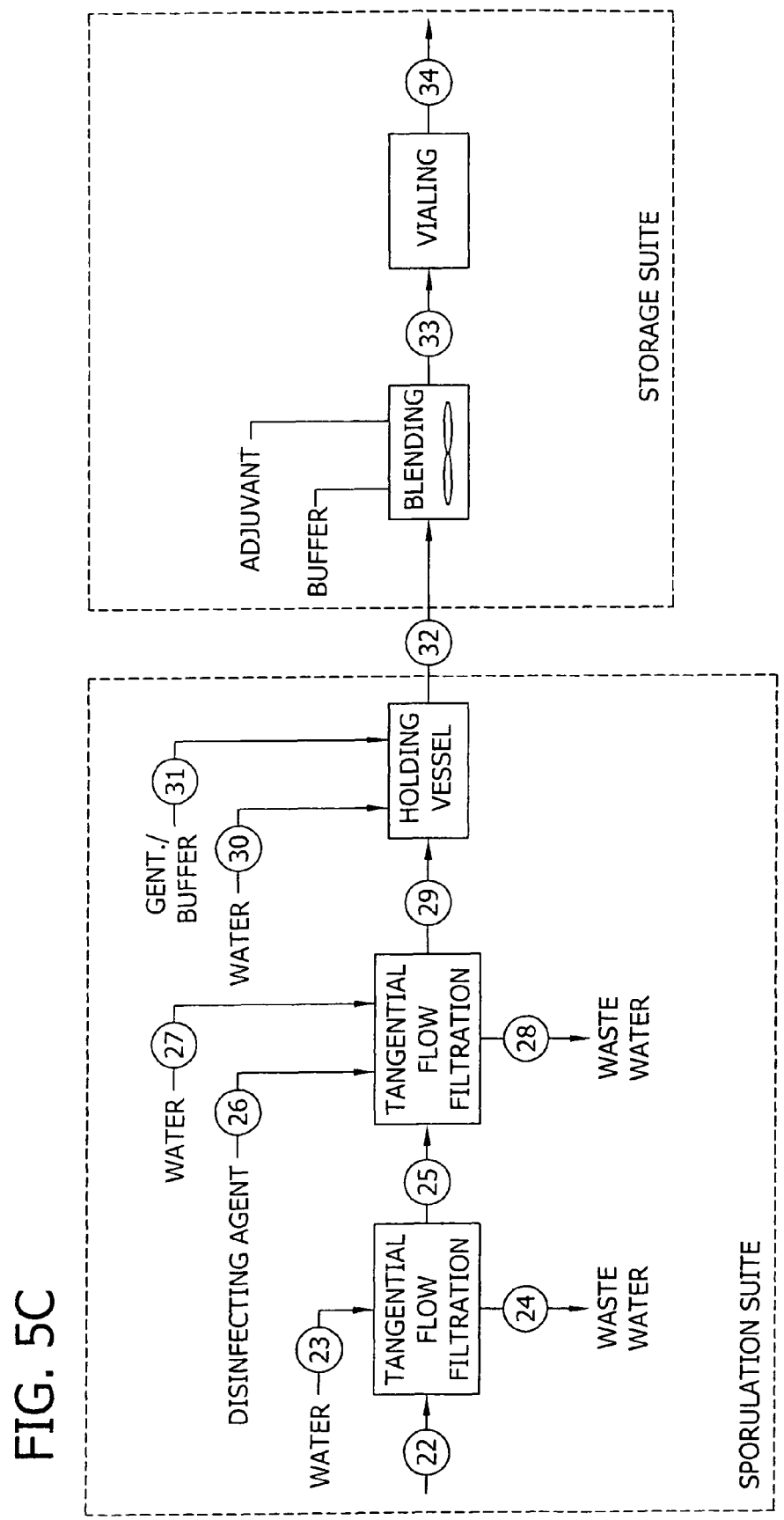

Following sporulation, the sporulated oocysts, are removed from the sporulation vessel, and washed free of the sporulation medium and concentrated by any suitable method, preferably filtration. The entire sterilization process is generally conducted in two phases: (1) contaminants are first removed non-aseptically (see FIG. 5C, steps 23-25); followed by (2) disinfection of sporulated oocysts medium carried out under sterile conditions (see FIG. 5C, steps 26-28). The purpose of this process is to collect sporulated oocysts and filter out contaminants. A further purpose is to concentrate oocysts, preferably by filtration. However, centrifugation may also be used to concentrate the sporulated oocysts. A further purpose is to sterilize the suspension with a disinfectant, preferably sodium hypochlorite (leaving the sporulated oocysts intact), then to remove the disinfectant from and then concentrate the sporulated oocysts. Then, to the sporulated oocysts, is added an appropriate quantities of buffer and antibiotic, preferably PBS and gentamicin (FIG. 5C, steps 30-31). This sporulated oocysts-containing suspension is then transferred into suitable storage containers for bulk storage prior to final packaging for distribution to consumers.

In one embodiment, separation of the sporulated oocysts from the sporulation medium may be achieved by centrifugal-based separation, such as by bottle centrifuge, decanter centrifuge, or by hydrocyclone. The volume of the batch size will be determinative of the mode of centrifugal-based separation and can be determined by one skilled in the art. The solid fraction from any one of the centrifugal-based separation methods is recovered. If more than about 5% of the oocysts loaded into the centrifugal-based separation unit are in the refuse fraction, a liquid fraction in this embodiment, said fraction is mixed with the solid fraction and recycled through the centrifugal-based separation unit. The recovered solids are then diluted to a volume appropriate for sterilization, preferably by filtration, more preferably by tangential flow filtration.

In a preferred embodiment, once sporulation is complete, the resultant aqueous suspension of sporulated oocysts is transferred from the fermentation vessel into a receiving vessel of appropriate volume. The transfer of the oocysts from the fermentation vessel is preferably accomplished by using air forced through the fermentation vessel, e.g., pressurizing the headspace, thereby forcing the sporulated oocysts into the awaiting container. A sample of the sporulation medium from the container is then taken to assess sporulated oocyst count and sporulation ratio. Any material still in contact with the fermentation vessel may be removed by using a rinse, e.g., a sufficient amount of domestic water, and the rinse may then be combined with the suspension of sporulated oocyst already transferred from the fermentation container (FIGS. 5B-C, step 22). Again, a sample is then taken to assess sporulated oocyst count and sporulation ratio in an effort to ascertain yield. The manner and method in which the sporulated oocysts are harvested from the fermentation vessel varies with the batch size and type of fermentation vessel and may be properly determined by one skilled in the art.

After removal of the suspension of sporulated oocysts from the fermentation vessel, the oocysts are allowed to settle from sporulation medium over a period of several hours, e.g., 8 to 20 hours, while the medium and the oocysts are held at a temperature from a temperature that prevents freezing to about 10° C., more preferably from about 2° C. to about 6° C., and most preferably about 4° C. Sporulated oocysts settle to the bottom of the storage container while contaminants remain suspended or dissolved in the aqueous layer. In a preferred embodiment, the supernatant is decanted, poured or pumped off using a small peristaltic pump or other method suitable to the volume being removed. Domestic water is then added at a sufficient volume to resuspend the sporulated oocysts. Settling can be carried out in the receiver or in a separate settling vessel.

The sporulated oocysts, now resuspended after collection from settling, are then separated from the sporulation medium. In a preferred embodiment, separation is by filtration. However, any appropriate means may be used to separate the sporulated oocysts from the sporulation media. In a more preferred embodiment, the filtration process is by means of tangential flow filtration. Tangential flow filtration ("TFF") is used in this procedure to separate sporulated oocysts from other material that may be present in the suspension, e.g., grit, other microorganisms, etc. In addition to the filter membrane, two essential parts of the TFF system are a retentate vessel, which holds the sporulated oocysts, and a low shear pump that circulates the retentate through the membranes and back into the retentate vessel. The oocysts are retained in the retentate while the permeate is discarded.

The pore size of the filter membrane should be small enough so that sporulated oocysts cannot enter the pores, but large enough to allow bacteria to pass through. In one embodiment, the filter has a pore size of approximately 10-microns. In yet another embodiment the filter has a pore size of approximately 5-microns. A preferred filtration unit is a CONSEP® membrane unit manufactured by North Carolina SRT (available from North Carolina SRT, Inc., 221 James Jackson Ave., Cary, N.C. 27513). However, other filtration units may be used, such as those produced by Millipore (available from Millipore Corporation, 80 Ashby Road, Bedford, Mass. 01730). A preferred filter is the SPECTRA/MESH® polyester filters (Spectrum Laboratories, Inc., Rancho Dominguez, Calif.; cat no: 146524). Tangential filtration units such as an OPTISEP CL®, OPTISEP®, or CONSEP® filtration unit may be used, also available from North Carolina SRT. Throughput can be increased by utilizing a larger scale filtration unit. One skilled in the art will recognize that the type of filtration unit needed depends on the volume of the sporulated oocyst suspension. In one embodiment, an OPTISEP CL® filtration unit is used to run about a 1 L sporulated oocyst suspension. In another embodiment, a CONSEP® filtration unit is used to run about a 10 L sporulated oocyst suspension.

When a filtration process is applied to a sporulated oocyst-containing medium the permeate is discarded. Water is added as permeate is removed if the filtration process is conducted at a constant volume. Filtration can be accomplished by gravity flow or by the use of a pump, for example, a peristaltic pump. In a preferred embodiment, the mixture is pumped tangentially over the filter. If a pump is used, the rate of pumping varies with such well known factors as the surface area of the filter, the path length, the total area of the flow channel, and the pore size. Optimum pumping rates can be determined by one of ordinary skill in the art without undue experimentation as such flow rates are a function of surface area of the filtration unit and solids content.

In a further embodiment, the inlet and the outlet tubing for the tangential flow unit are placed into a vessel containing the sporulated oocysts while the permeate tubing is placed in a separate vessel. The pump, for example, a diaphragm pump, is then started to begin filtration. A preferred flow rate is about 1 LPM per 160 $cm^2$. The pump rate may also be expressed in terms of lineal velocity. Lineal velocities may be between 20 and 50 centimeters per second. A preferred lineal velocity when using a CONSEP® filtration unit is 28 centimeters per second. The pump may be kept running to maintain the flow rate throughout the process. The permeate is sampled and, using a glass slide, observed for sporulated oocysts. The optical density of the permeate sample is also measured using a spectrophotometer at 600 nm ($OD_{600}$). Circulation of retentate over the filter medium is continued if the concentration of oocysts in the permeate has not increased to or exceed a maximum tolerable level. An acceptable concentration is from about not more than 5% of the total sporulated oocysts loaded into the filtration unit. If the sporulated oocysts concentration measures to or above the maximum acceptable level, filtration is stopped. The permeate is recycled and mixed with the retentate and filtration is resumed. Filtration is stopped when the measured $OD_{600}$ is about less than about 0.5 at a lineal velocity of about 28 centimeters per second. However, filtration may be stopped when the measured $OD_{600}$ is about 0.6, again at a lineal velocity of about 28 centimeters per second. Once the desired OD is reached, oocysts from the membranes and the tubing are transferred to the retentate vessel and any oocysts remaining in the membranes and tubing are then flushed with water into the retentate vessel.

The retentate, containing the concentrated oocysts, is then placed in a vessel under refrigeration at about 4° C. from about 15 to about 24 hours. This allows the sporulated oocysts to settle in bottom solid phase and a liquid phase will normally form above the solid phase. The liquid phase is then substantially removed after refrigeration to reduce unwanted volume, e.g., by decanting, pumping, or siphoning. In an alternative embodiment, the retentate is processed immediately after filtration. However, it is preferred to let the retentate rest as described above.

Once the sporulated oocysts have been concentrated by filtration they can be sterilized by means of a chemical disinfectant or sterilizing agent other than an alkali metal dichromate, soluble dichromate moieties, dichromate ions, or potassium dichromate. Sterilization processes are conducted in sterile environments. In a preferred embodiment, sterilization is accomplished within the filtration device used to concentrate the sporulated oocysts. In an alternative embodiment the retentate containing the sporulated oocysts can be washed from the filter and sterilization is accomplished in a vessel separate from the filtration device. Any filtration unit used to sterilize the sporulated oocysts should be sterilized prior to the addition of the unsterilized sporulated oocysts. In one embodiment, the filtration unit is sterilized by autoclaving. In an alternative embodiment, the filtration unit is sterilized by passing steam at approximately 250° C. through the system for at least about 30 minutes at approximately 20 psi. In yet another alternative embodiment, the unit is chemically sterilized by treating the system with 5% sodium hypochlorite for at least about 10 minutes wherein the sodium hypochlorite contains at least about 5% available chlorine by weight.

The agent used for sterilizing the sporulated oocysts preferably is one which kills bacteria and viruses, but does not kill the sporulated oocysts. Preferably, the disinfectant used kills the infectious bursal disease (IBDV), chick anemia (CAV) viruses, and related bacteria. As IBDV is known to be a robust virus, a sterilization agent that kills IBDV will kill other, less robust microorganisms as well. An agent that eliminates IBDV is considered to substantially eliminate microorganisms.

In a preferred embodiment, the disinfectant used is sodium hypochlorite. The concentration of disinfectant used varies with the agent chosen to accomplish sterilization. In more preferred embodiment, sodium hypochlorite is used at a concentration preferably in the range from about 1% to about 10%, and more preferably in the range of about 2% to about 5% wherein the percent represents the percent of available chlorine by weight. The time during which the sporulated oocysts are exposed to the disinfectant varies depending upon factors such as the concentration of the disinfectant and the volume of the batch of sporulated oocysts. In one embodiment, the sporulated oocysts are treated with approximately 5% sodium hypochlorite, wherein the percent represents the percent of available chlorine by weight, from about 2 to about 20 minutes, more preferably from about 5 to about 18 minutes, and most preferably for about 10 minutes.

Once the filtration unit is sterilized, the vessel holding the sporulated oocyst suspension is then removed from refrigeration. The clear upper layer is removed by pumping, pouring, or suctioning off the supernatant, leaving the bottom sporulated oocyst fraction. The latter fraction is then transferred to a retentate vessel of adequate volume. The previous vessel is then rinsed with domestic water. The domestic water rinse is then added to holding vessel and stirred by adequate means. In one embodiment, stirring is accomplished by means of a magnetic stir bar while the retentate vessel is sitting on a magnetic stirrer. In another embodiment, stirring is accomplished by means appropriate for the volume of the retentate vessel, such as with a paddle.

Next, a volume of about 10% aqueous sodium hypochlorite solution that is approximately equal to the volume of suspension in the retentate vessel is added to the sporulated oocyst suspension. The sporulated oocyst suspension containing sodium hypochlorite should have a solids content of preferably less than about 30%, more preferably to less than about 25%, and even more preferably to less than about 15%, and most preferably to less than 7.5%. A solids content of less than about 7.5% is preferred as the reduced solids content produces a higher assurance of sterility. When solids are brought to about 15%, there is approximately 5% sodium hypochlorite, wherein the percent represents the percent of available chlorine by weight, in the suspension. In an alternative embodiment, the solids concentration is adjusted to about 15% prior to sodium hypochlorite addition. After this addition, the solids are 7.5% and the sodium hypochlorite is at 5%. With either embodiment, the suspension is mixed thoroughly by adequate means and, in one embodiment, allowed to stand for preferably 5 minutes, more preferably 8 minutes, and most preferably about 10 minutes. Standing time will vary depending on batch size and volume and may be adjusted as needed. However, standing may be avoided and filtration may occur immediately after dilution.

The retentate vessel containing the sporulated oocysts suspension is then connected to the filtration unit. Autoclaved or otherwise sterile water is used as a water source during the sterilization process. The retentate pump is then activated while the permeate line is pinched or clamped closed. Once any air bubbles have been substantially eliminated from the membranes and tubing the permeate line may be opened and directed to a collection vessel outside a sterile environment. Permeate is then analyzed to verify that there is no significant loss of oocysts via the permeate.

In an alternative to using filtration to remove the sodium hypochlorite from the oocyst suspension, centrifugation may be utilized.

While the hypochlorite-rich permeate leaves the filtration unit, sterile water is added to replenish the volume. Filtration is continued and water is added as needed to control the percent solids during filtration. A sample is then taken from the permeate to determine total chlorine level. Chlorine level can be detected using chlorine detection kits, such as those available from CHEMetrics, Inc., Route 28, Calverton, Va., 20138. The total level of chlorine should is reduced to less than about 1 ppm. When the permeate contains less than about 1 ppm of the chlorine the retentate, which contains the oocysts, also contains less than about 1 ppm. Once the desired level of chlorine is reached, filtration may be continued without adding more water to reduce the overall volume of the sporulated oocysts suspension.

When the desired retentate volume is reached, the pump feed tubing is removed from the retentate vessel and placed into a vessel containing sterile water and filtration is continued. Once substantially all of the suspension has been flushed out of the tubing and the filter housing, the pump is shut off and filtration is complete.

Next, if desired, a buffer, such as PBS, and a bactericide is added to the sterilized sporulated oocyst suspension. In a preferred embodiment, 1×PBS containing 60 μg/ml gentamicin is added in a 1:1 ratio to the disinfected sporulated oocyst suspension to result in a suspension of sporulated oocysts in 0.5×PBS with 30 μg/ml gentamicin. The suspension is then stored under refrigeration, preferably around 4° C. for future use. In an alternative embodiment, 1×PBS is added to the sporulated oocyst suspension while no bactericide is added to the sporulated oocyst suspension. Average yields for all three subspecies, *E. tenella, E. acervulina*, and *E. maxima*, is about 70% for disinfection and final filtration.

For the purposes of the present invention, sporulated oocysts and compositions containing sporulated oocysts are considered sterile if samples of liquids containing the oocysts do not have detectable amounts of live bacteria, IBD virus or CAV virus. Detection of live bacteria can be accomplished by any method known in the art. For example, bacteria can be detected by incubation on bacterial agar plates at 35-37° C. for 18 to 24 hours. One preferred method of testing is set forth by the USDA in 9 C.F.R. 113.27 (1999), hereby incorporated in its entirety by reference. Briefly, to test for bacterial contamination, a sample of the preparation of the present invention can be innoculated into soybean casein digest medium and incubated at 30 to 35° C. for 14 days. To test for fungal contamination, a sample of the preparation of the present invention can be innoculated into soybean casein digest medium and incubated at 20 to 25° C. for 14 days. After the incubation period, the vessels can be examined macroscopically for microbial growth. If growth cannot be determined reliably by visual examination, the judgment can be confirmed by microscopic examination.

Detection of IBDV virus or CAV virus can be by any method known in the art. A non-limiting example of IBDV and CAV detection is by the methods set forth by the USDA in 9 C.F.R. 113.47 (1999), herein incorporated in its entirety by reference. Briefly, to test for CAV, MSB-1 cells from the Maine Biological Laboratories, Waterville, Me. are used as the indicator cell line for Chicken Anemia Virus. MSB-1 cells are a lymphoblastoid cell line from a Marek's disease lymphoma that show cytopathic effect when infected with Chicken Anemia Virus. Cells are maintained in a medium, such as OPTI-MEM® (Life Technologies, Gaithersburg, Md.) or other suitable media at 41° C. for at least 24 days prior to testing. Cells are subcultured 10-12 times during the maintenance period with all but the last subculture resulting in a monolayer of at least 75 cm². The last subculture is at least 6 cm².

Three groups of MSB-1 monolayers are used for each test, a negative control group, a positive control group, and a test group. At the start of the 24 day maintenance period, the positive control group is inoculated with $10^{5.75}$ TCID$_{50}$/ml of Chicken Anemia Virus, Del Ros strain originally obtained from the Center for Veterinary Biologics Laboratory (Ames, Iowa) and the test group inoculated with the test preparation. The negative control group is inoculated with a preparation known to be free of Chicken Anemia Virus. The cells are then maintained for at least 24 days as described above.

Two days after the last subculture, the three groups of monolayers are fixed and treated with a specific chicken polyclonal Chicken Anemia Virus antibody (Hy-Vac, Adel, Iowa). The monolayers are then washed and treated with a fluorescein labeled goat anti chicken IgG (H&L, Jackson Immunoresearch, West Grove, Pa.) and examined for specific fluorescence. If the positive control shows specific fluorescence and there is no difference in fluorescence between the test and negative control groups, the preparation is considered free of Chicken Anemia Virus.

Alternatively, the presence of Chicken Anemia Virus can be detected by the polymerase chain reaction (PCR). Three days after the last subculture, DNA is extracted from the three groups of monolayers using well established procedures. See, for example, Ausubel et al., *Short Protocols in Molecular Biology*, 2$^{nd}$ Ed., John Wiley & Sons, 1992; Sambrook et al., *Molecular Cloning, A Laboratory Manual*, 2$^{nd}$ Ed., Cold Spring Harbor Laboratory Press, 1989; Davis, et al., *Basic Methods in Molecular Biology*, Elsevier, 1986. Briefly, cells are lysed by two cycles of freezing to −80° C. and thawing at 37° C. Cellular debris is removed by centrifugation at about 3,500×g for 20 minutes. The supernatant is treated with DNase and RNase A to remove cellular contaminants and the proteins and/or virus precipitated with polyethylene glycol. The precipitate is treated with Proteinase K and extracted three times with phenol/chloroform/isoamyl alcohol. DNA is precipitated with sodium acetate-ethanol and pelleted by centrifugation at 14,000×g for 15 minutes. The resulting pellet is resuspended in double distilled water and stored at −20° C.

Conserved regions of the Chicken Anemia Virus viral genome are amplified using standard techniques (Innis et al., *PCR Protocols*, Academic Press, 1990). Information on the Chicken Anemia Virus viral genome for designing suitable primers can be found on databases well known to those in the biomedical arts such as the databases available through the website of the U.S. National Institutes of Health. PCR products are analyzed by agarose gel electrophoresis and ethidium bromide staining. If the PCR amplification does not result in a band corresponding to the band found in the positive control, the preparation is considered free of Chicken Anemia Virus.

One preferred, but non-limiting method for detection of IBDV in the preparation of the present invention is the same as for Chicken Anemia Virus with the following changes. A preferred cell line used for IBDV testing is a primary chick embryo fibroblast cell line. After addition of a sample of the preparation or $10^{8.25}$ TCID$_{50}$ of IBDV originally obtained from American Type Culture Collection (ATCC VR-2041 strain D78), the monolayers are maintained in basal medium Eagle (BME) or other suitable media at 37° C. and 5% $CO_2$ for at least 14 days. Detection is preferably accomplished using an IBDV specific polyclonal chicken antiserum and a fluorescein labeled goat anti-chicken IgG (Jackson Immunoresearch, West Grove Pa.). If the positive control shows specific fluorescence and there is no difference in fluorescence between the test and negative control groups, the preparation is considered free of IBDV.

Alternatively, the test for the IBDV contamination can be accomplished using PCR as described for Chicken Anemia Virus. Information on the IBDV viral genome for designing suitable primers can be found on databases well known to those in the biomedical arts such as the databases available through the website of the U.S. National Institutes of Health. If the PCR amplification does not result in a band corresponding to the band found in the positive control, the preparation is considered free of Infectious Bursal Disease Virus.

Post-challenge performance improvement compositions may also be added to the sterilized sporulated oocyst suspension. A preferred post-challenge performance improvement composition is *Propionibacterium acnes* (*P. acnes*) and can be added to the sporulated oocyst suspension prior to the time of filling vials for consumer use. The *P. acnes* may be obtained from independent manufactures in 1-liter glass bottles suspended in PBS or water and having gentamicin at a cell density equivalent to $10^{12}$ cells/ml of the pre-autoclaved *P. acnes* count. The *P. acnes* suspension is preferably included in the final vaccine at a dry weight dose equivalent to 50 µg per bird.

Storage

The instant invention also provides for compositions to store sterile sporulated oocysts. The sporulated oocysts can be held in sterile water or other suitable diluent (see FIG. 5C, "Storage Suite"). In a further embodiment, an oxidizing agent is added to the storage composition. In one embodiment, the suspension of sporulated oocysts is transferred to vials that are prepared in a kit containing the suspension as a ready-to-administer vaccine.

Sterile sporulated oocysts are preferably stored at any temperature between room temperature and a low temperature that substantially avoids freezing. In a preferred embodiment, the sporulated oocysts are stored at between about 1° C. and about 10° C., more preferably between about 2° C. to about 7° C., and in a most preferred embodiment between about 4° C. to about 5° C. In an alternative embodiment, the sporulated oocysts are stored at a temperature between 20° C. to about 30° C., more preferably between 22° C. to about 27° C., and most preferably at about 25° C.

Although not necessary, a buffering agent may be added to the diluent in which the sporulated oocysts are stored. Buffers are utilized in the storage composition as they prolong viability over the use of sterile water or sterile water containing gentamicin. Many suitable buffers are known in the art including, but not limited to, phosphate buffer, bicarbonate buffer, citric acid and tris buffers. In one preferred embodiment, the diluent comprises 0.5×PBS. In a preferred embodiment, a volume of buffer is used that results in a concentration of sporulated oocysts suitable for transfer to containers that are ultimately used by the consumer as a vaccine for the prevention of coccidiosis.

The diluent may also optionally comprise a bactericide or other preservative. Any bactericide that is suitable for use in pharmaceutical compositions, and especially compositions that are administered to food animals, can be used. Non-limiting examples or bactericides include potassium perchlorate, sodium hypochlorite, hydrochlorous acid, sodium hydroxide and antibiotics. Preferred concentrations of chemical bactericides in final concentration in the vaccine, include: from about 0.10 wt % to about 0.25% potassium perchlorate, from about 0.001 wt % to about 0.01 wt % sodium hypochlorite, from about 1 ppm to about 5 ppm hydrochlorous acid, and from about 0.5 mM to about 1 mM sodium hydroxide. In another aspect of the instant invention, any antibiotic which is suitable for incorporation into compositions to be administered to animals, and especially food animals can be used.

In one embodiment, after the sterilization and final concentration, rather than adding water back to 100% of the volume prior to sterilization in the filtration unit, the volume is brought back up to 50% of the volume prior to sterilization and filtration. In this particular embodiment, the tangential flow filter and associated tubing are flushed with a sterile PBS buffer solution to collect any residual sporulated oocysts and the rinse is added to collected retentate. In a preferred embodiment, 1×PBS containing 60 µg/ml gentamicin is added in a 1:1 ratio to the disinfected sporulated oocyst suspension to result in a suspension of sporulated oocysts in 0.5×PBS with 30 µg/ml gentamicin. A sample is then taken for assay purposes. Thereafter, the material is subdivided into pre-sterilized containers, sealed, labeled and stored in the cold room pending filling of containers for commercial distribution, such as vials. This material constitutes a bulk lot.

In yet another embodiment, the diluent used for storage purposes includes a composition that ameliorates a decrease in post-challenge performance and thickening agents to maintain the sporulated oocysts in suspension. Suitable thickening agents include starches, gums, polysaccharides, and mixtures thereof. Suitable compositions to ameliorate a decrease in post-challenge performance include, but are not limited to, cytokines, growth factors, chemokines, mitogens and adjuvants. Such compositions to improve post-challenge performance are well known to those skilled in the art and can be found, for example, in Plotkin and Orenstein, *Vaccines*, Third Ed., W.B. Saunders, 1999; Roitt et al., *Immunology*, Fifth Ed., Mosby, 1998; and Brostoff, et al., *Clinical Immunology*, Gower Medical Publishing, 1991. Examples of compositions to improve post-challenge performance, include, but are not limited to, Alum (aluminum phosphate or aluminum hydroxide), Freund's adjuvant, calcium phosphate, beryllium hydroxide, dimethyl dioctadecyl ammonium bromide, saponins, polyanions, e.g. poly A:U, Quil A, inulin, lipopolysaccharide endotoxins, liposomes, lysolecithins, zymosan, propionibacteria, mycobacteria, and cytokines, such as, interleukin-1, interleukin-2, interleukin-4, interleukin-6, interleukin-12, interferon-α, interferon-γ, granulocyte-colony stimulating factor. In one preferred embodiment, the diluent includes *Propionibacterium acnes* (*P. acnes*) at from between 10 µg and 100 µg per dose (dry weight) and more preferred at about 50 µg per dose (dry weight). The preferred concentration is from about 3.0 to about 5.0 milligrams per milliliter of vaccine, most preferably about 4.2 milligrams per milliliter.

In a further embodiment of the present invention, sterile sporulated oocysts are stored in a composition comprising an oxidizing agent. The oxidizing agent preferably has a reduction potential of greater than 0.5 V, more preferably between 0.75 and 3.0 V, most preferably between about 1.0 and 2.0 V in the sporulation medium. The oxygen present in sterile water may also be used as the oxidizing agent. When sterile water, or any other oxidizing agent is used, no additional oxygen or air is incorporated in to the storage composition. Examples of other suitable oxidizing agents include, but are not limited to, aqueous bromine, chlorine dioxide, hydrogen peroxide, potassium permanganate, potassium perchlorate, sodium hypochlorite, and hydrochlorous acid which have reduction potentials of about 1.09 V, 1.64 V, 1.78 V, 1.49 V, 1.37 V, 1.49 V, and 1.63 V, respectively. The requisite amount of oxidizing agent added varies with the agent used and the species of protozoa and can be determined empirically by one skilled in the art. For protozoa of the genus *Eimeria*, preferred concentrations of the oxidizing agents once added to the sporulated oocyst suspension include from about 0.1 to about 0.75 wt % for potassium perchlorate, from about 0.5 to about 2.9 wt % for potassium permanganate, from about 0.001 to about 0.1 wt % sodium hypochlorite and from about 1 ppm to about 5 ppm for hydrochlorous acid.

In one embodiment, the sporulated oocysts in contact with the diluent retain greater than 60% viability when stored for 13 weeks at 25° C. In a preferred embodiment of the instant invention, the sporulated oocysts in contact with the diluent retain greater than 70% viability for at least 26 weeks when stored at 4° C. Because the resulting vaccine is sterile and lacks potassium dichromate, the product is suitable for administration by a variety of routes including, but not limited to, intravenous, subcutaneous, intramuscular and intraperitoneal injection. Thus, the sporulated oocyst/diluent composition can be used for vaccinating animals against coccidiosis.

The instant invention comprises a composition containing viable sporulated oocysts of a single species or combination of species of protozoa known to coccidiosis. The combined species of sporulated oocysts are present in a number sufficient to comprise the minimum number of sporulated oocysts required to comprise an effective dose for immunizing purposes. The number of sporulated oocysts per dose is further determined by the estimated half-life of the sporulated oocysts in the storage composition claimed herein. As the sporulated oocysts age a certain number cease to be functional. A preferred shelf-life is approximately 12 months. An example of half-life determinations may be found in FIGS. 4 and 5 and Example 4. Therefore, a minimum amount of a single species or combination of sporulated oocysts is added to the compositions for consumption that will result in the minimum immunizing dose computed as a function of half-life determinations.

The storage medium of the current invention contains less than about 0.8% by weight of alkali metal dichromate. In more preferred embodiments, the instant invention contains less than about 0.6% by weight of alkali metal dichromate, or less than about 0.4% by weight of alkali metal dichromate, or less than about 0.2% by weight of alkali metal dichromate, and less than about 0.1% by weight of alkali metal dichromate.

Again, as the production of the concentrated vaccine is without the use of an alkali metal dichromate, the storage composition will contain less than about 0.3% by weight of dichromate ion. In another embodiment, the storage composition of the instant invention will contain less than about 0.15% by weight of hexavalent chromium.

Furthermore, a most preferred embodiment of the instant invention comprises a coccidiosis vaccine for chickens using the sporulated oocyst/diluent composition of the present invention containing at least about $1.5 \times 10^4$ viable wild type sporulated oocysts per milliliter and is characterized as substantially free of potassium dichromate.

In addition, a dye may be added to the vaccine to encourage consumption. Dyes well known in the art may be used. A preferred dye is 0.02% FD+C Emerald Green.

Vaccine Composition

The present invention also provides a vaccine composition for the prevention and control of coccidiosis. The vaccine may be concentrated, requiring dilution before administration, or the vaccine may be ready for administration. The concentrated embodiment of the instant invention may be diluted with any suitable diluent to concentrations suitable for various forms of administration, including intra-yolk sac administration, per os, oral gavage, delivery via spray cabinet, or top-fed via spray on to food, such as OASIS Hatchling Supplement.

The vaccine composition of the instant invention comprises wild type sporulated oocysts of at least one species of protozoa known to cause coccidiosis wherein said composition is sterile and contains at least about 10,000 oocysts per milliliter and less than about 0.8% by weight of alkali metal dichromate. In more preferred embodiments, the instant invention contains about 10,000 oocysts per milliliter and less than about 0.6% by weight of alkali metal dichromate, or about 10,000 oocysts per milliliter and less than about 0.4% by weight of alkali metal dichromate, or about 10,000 oocysts per milliliter and less than about 0.2% by weight of alkali metal dichromate, or about 10,000 oocysts per milliliter and less than about 0.1% by weight of alkali metal dichromate. In addition, the vaccine composition of the current invention will contain at least about 10,000 oocysts per milliliter and less than about 3.0% by weight of dichromate ion or less than about 0.15% by weight of hexavalent chromium.

In a further embodiment, the concentrated vaccine may be diluted prior to administration, for example, from 10 milliliters to about a 250 milliliter. In another embodiment, the concentrated vaccine may be diluted prior to administration from about 10 milliliters to about 2.5 Liters. Such dilute vaccine is sterile and comprises wild type oocysts known to cause coccidiosis. In a preferred embodiment, said diluted vaccine composition comprises at least about 1,000 oocysts per milliliter and less than about 0.002% by weight of alkali metal dichromate. In a more preferred embodiment, said diluted vaccine comprises at least about 1,000 oocysts per milliliter and is characterized as substantially free of alkali metal dichromate.

In a most preferred embodiment, the instant invention is a concentrated vaccine ready for dilution and then administration wherein said concentrated vaccine contains at least about 10,000 sporulated viable wild type oocysts per milliliter and is characterized as substantially free of alkali metal dichromate.

The vaccine composition of the present invention also comprises viable wild type sporulated oocysts containing less than about $5.0 \times 10^{-3}$ µg of alkali metal dichromate per oocyst. In a preferred embodiment the vaccine composition contains less than about $3.8 \times 10^{-3}$ µg of alkali metal dichromate per oocyst. In a more preferred embodiment the vaccine composition contains less than about $1.3 \times 10^{-3}$ µg of alkali metal dichromate per oocyst. In a highly preferred embodiment the vaccine contains less than about $6.3 \times 10^{-5}$ µg of alkali metal dichromate per oocyst. In a most preferred embodiment the vaccine composition is characterized as substantially free of alkali metal dichromate.

EXAMPLES

The following examples are intended to provide illustrations of the application of the present invention. The following examples are not intended to completely define or otherwise limit the scope of the invention.

Example 1

Oocyst Collection and Isolation

Five hundred fifty, 15 day old broiler chickens were infected with approximately 7000 viable oocysts per bird of *E. tenella* by oral gavage or by ingestion via drinking water or feed. Excreta were collected over a three day period beginning 6 days later at 21 days of age. Total excreta collected over the three day period was 189 kg. Excreta were processed on the day collected. The excreta collected were put in a dilution tank maintained at approximately 40-50° F. and diluted with water at 0.687 to 0.630 L/bird. The diluted excreta was pumped through a 30" diameter vibrating sieve fitted with a 50 mesh (297 micron) top screen and a 250 mesh (61 micron) bottom screen at a rate of approximately 6 LPM. The top two fractions were discarded and the filtrate, containing the oocysts, was pumped into a chilled (about 40-50° F.) collection tank and continuously agitated. The filtrate was then pumped at a feed rate of approximately 2.9-3.5 LPM into a Sharples Super-D-Canter centrifuge. The centrifuge settings were: bowl speed 3990-4004 RPM; auger speed 2306-3990 RPM and RPM delta 16.84-17.33. RPM delta is a measure of the difference between bowl and auger speeds. Total run time ranged from 97 to 100 minutes. The centrate was discarded and the solids (cake), which contained oocysts, were collected into a stainless steel tray, weighed and stored in a tank at about 40-50° F. The solids obtained from each of three collection days were combined.

The volume of solids from the combined three runs was 28 L. To these solids was added 25.6 L of high fructose corn syrup and 46.4 L of water to give a total volume of 100 L and a specific gravity of 1.094 g/l. This material was then centrifuged using a Sharples Super-D-Canter centrifuge at a bowl speed of 5998 RPM, an auger speed of 3998 RPM and a RPM delta of 20.41. The feed rate was 1.1 l/min and the total run time was 95 minutes. The centrate, containing the oocysts, was collected and stored in a tank at approximately 40-50° F. and the unwanted excreta solids discarded.

In order to remove the residual sugar in solution and to concentrate the oocysts further, the centrate was subjected to an additional centrifugation. To the 96 L of centrate obtained was added 114 L of water to give a final volume of 210 L. The centrifuge settings were bowl speed 6011 RPM and auger speed 4050 RPM. The initial RPM delta was 20.01 but was decreased to 15 and then 10 during the run to increase centrate flow. The centrate was discarded and the solid containing the oocysts was retained. The oocysts were placed in a sterilized container with sterile water at a preferred concentration of between about $5 \times 10^6$/ml and about $50 \times 10^6$/ml and held at from about 2° C. to about 8° C. until transferred to the sporulation vessel to undergo sporulation.

Example 2

Separation by Hydrocyclone

The manure from 400 host birds inoculated with *E. maxima* was collected from a one day period resulting in 45 kg of manure. This manure was diluted and sieved according to the method of Example 1 to give a filtrate volume of 270 L containing 6% solids and $4.64 \times 10^9$ oocysts. The filtrate was then introduced to the hydrocyclone by a high pressure pump at a feed rate of approximately 2 gallons per minute and at a pressure of 126 psi.

The first run resulted in the an upper outlet volume (overflow) of 182 L containing $1.58 \times 10^8$ oocysts and a lower outlet volume of 88 L containing 8% solids and $4.02 \times 10^9$ oocysts. Overflow material was discarded after each run. A second run resulted in an upper outlet volume of 56 L containing $1.46 \times 10^8$ oocysts and a lower outlet volume of 28 L containing a 13% solids and $3.25 \times 10^9$ oocysts. A third and final run resulted in an overflow volume of 18 L containing $1.27 \times 10^8$ and a final volume for the lower outlet of 10.5 L containing 27% solids and $3.56 \times 10^9$ oocysts.

Example 3

Sporulation

Figure 1B:
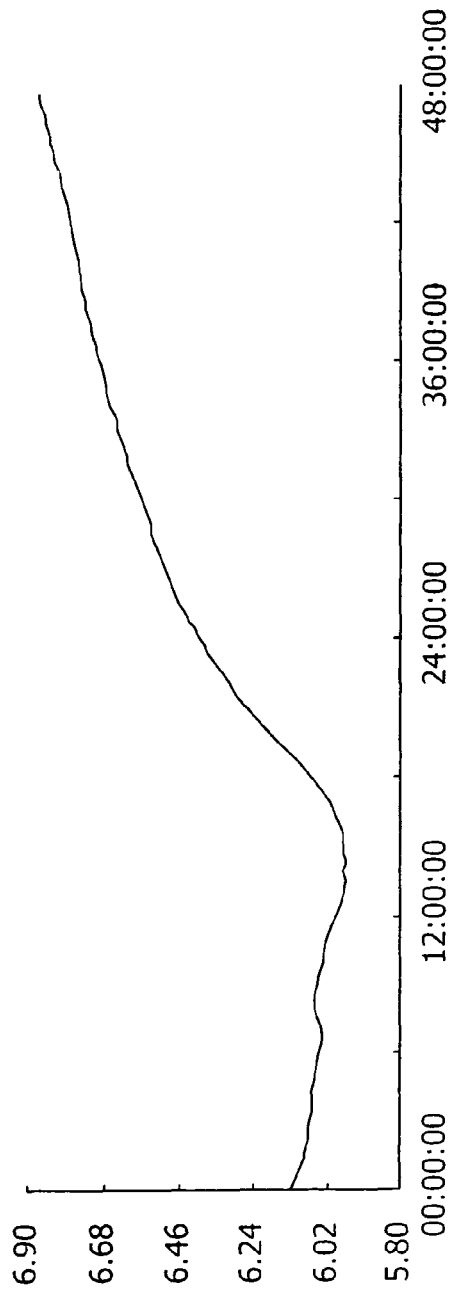
Figure 2A:
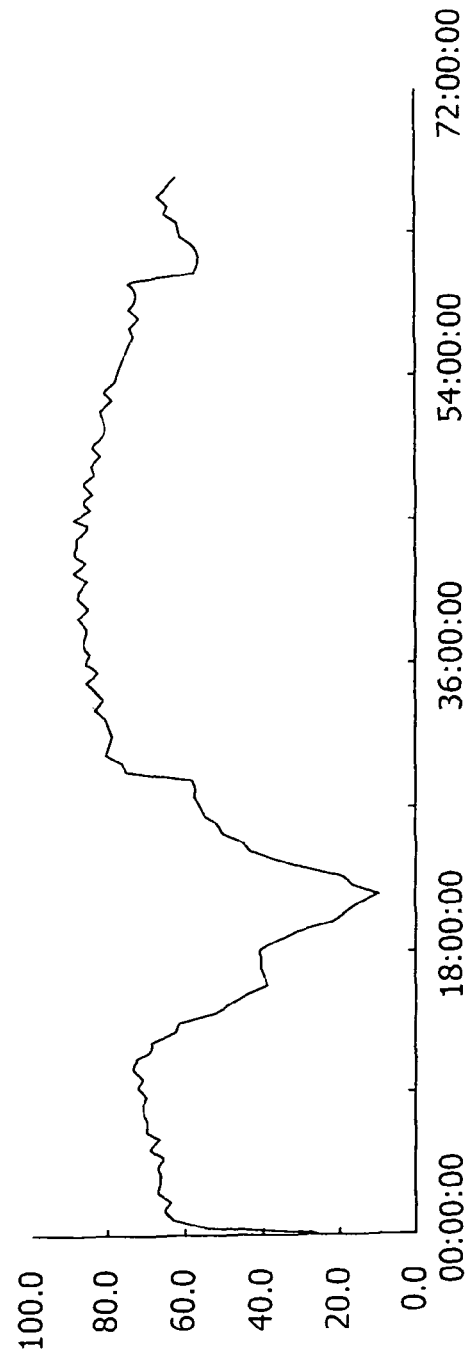
FIG. 2 shows a graph of percent saturation of dissolved oxygen (A) and pH (B) versus time of the sporulation medium during a successful sporulation in which the rise in pH was preceded by a drop in pH when percent saturation of dissolved oxygen and pH is not controlled.
Figure 2B:
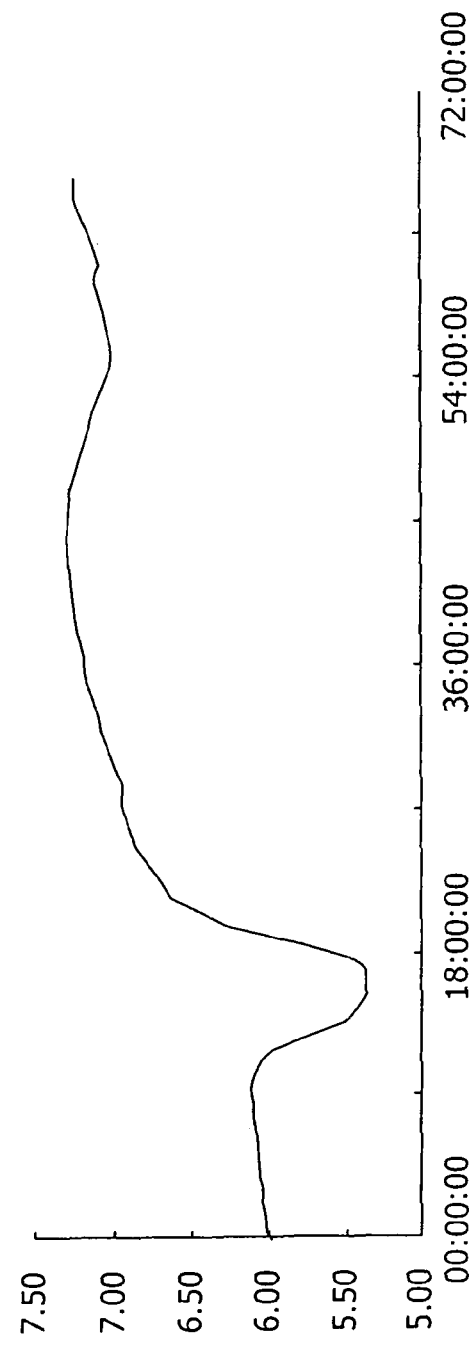

To the oocysts obtained as described in Example 1, was added enough of a 5.25% sodium hypochlorite solution to obtain a final concentration 0.05 wt % sodium hypochlorite. This oocyst/sodium hypochlorite mixture was added to a 10 liter fermentor set at $28 \pm 1°$ C. and an agitation rate of 200 RPM. Oxygen was provided by portable oxygen cylinders and bubbled through the mixture at a rate sufficient to obtain a percent saturation of dissolved oxygen value of at least 50% of saturation of dissolved oxygen. Oxygen flow was adjusted so as not to cause foaming of the mixture. The oocysts were maintained under these conditions for about 72 hours. During sporulation, dissolved oxygen and pH were constantly monitored. It was observed that beginning at approximately 12 hours into the sporulation process there was a decrease in the percent saturation of dissolved oxygen (increased oxygen consumption) followed by an increase in pH and a return of dissolved oxygen to previous levels (FIG. 1). In some, but not all cases, the increase in pH was preceded by a decrease in pH at about the same time as the decrease in the percent saturation of dissolved oxygen (FIG. 2). These changes in dissolved oxygen and pH were found to be reliable indicators of sporulation. Examination of oocysts following these change showed a high degree of sporulation. In contrast when these changes were not observed, the sporulation rate was dramatically reduced from approximately 90% to approximately 10%. Although sporulation was complete at approximately 24 to 36 hours, the incubation was continued for another 36 to 48 hours to provide a more stable sporulated oocyst population.

Oocyst quantities for individual species are approximately as follows:

TABLE 2

| Spp. of Eimeria | Quantity |
| --- | --- |
| E. acervulina | 22 million/mL |
| E. maxima | 13.6 million/mL |
| E. tenella | 13.7 million/mL |

The average oocyst sporulation ratio determined for individual species was as follows:

TABLE 3

| Spp. of Eimeria | Percent average sporulation ratio |
| --- | --- |
| E. acervulina | 80% |
| E. maxima | 90% |
| E. tenella | 90% |

The average oocyst viability determination for individual species was as follows:

TABLE 4

| Spp. of Eimeria | Average oocyst viability |
| --- | --- |
| E. acervulina | 80% |
| E. maxima | 70–80% |
| E. tenella | 80% |

Example 4

Tangential Flow Filtration/Sterilization

Following sporulation, the sporulated oocysts were concentrated by tangential flow filtration. To begin, the integrity of the filter membrane was visually observed prior to assembling the CONSEP® tangential flow filtration system. The filter unit was then assembled according to the appropriate standard operating procedure ("SOP") as provided in the manufacture's manual. After the system was assembled about 2 to 4 liters of cold domestic water was run through the system to check for leaks. If leaks were found, the system would be disassembled and reassembled after checking for the source of the leakage. Particular attention was paid to inspecting the gaskets to assure lack of damage to the gaskets and for proper seating.

The concentrated sporulated oocysts medium was then placed into the retentate vessel of the filter unit. Domestic cold water was added to adjust the retentate vessel volume to the desired operating level and also maintain less than a desired amount of solids. The water source was then connected to the retentate vessel through an air-tight fitting. This facilitates operating diafiltration at a constant volume.

The permeate flow valve was then closed. The control of the diaphragm pump was set to give the desired flow and then the pump was started. The permeate flow valve was then opened after substantially all of the bubbles were removed from the membranes and a steady flow was established across the membrane. The permeate was then directed to a separate collection container. The permeate sample was collected after about 2 to 5 minutes of operation and checked for sporulated oocysts. The sporulated oocysts are to be retained in the system. If sporulated oocysts were found in the permeate, the filtration would have been stopped and the source of retentate leakage identified. Retentate leakage often occurs from gaskets around the membrane or when the integrity of the membrane is compromised. The source of a leak must be detected and corrected before proceeding with permeation. Permeate collection, found to be without sporulated oocysts, was then discarded. If sporulated oocysts were found, the permeate would have been returned to the filter unit to recover any sporulated oocysts that may have leaked through into the permeate.

The flow rate of the permeate was checked periodically by measuring the volume of permeate by collecting the permeate in a graduated cylinder. The retentate tank volume was maintained at a constant volume. A small sample of the permeate was collected after every 2 liters of permeate was collected from the permeate line and the optical density at 600 nm ($OD_{600}$) was measured. Once the $OD_{600}$ of the permeate was less than 0.5, the diafiltration was stopped by closing the permeate value and disconnecting the water source. The pump's inlet lines were then removed from the retentate vessel and connected to a clean water source. The membrane were then flushed with about 500 to about 1000 ml of water to recover any sporulated oocysts. The retentate vessel was then stored overnight at about 4° C. in a refrigerator. The retentate was stored overnight to allow the sporulated oocysts to settle to the bottom of the retentate vessel. The layer of retentate over the settled oocysts was then siphoned off.

The sporulated oocysts were then sterilized. The filter unit was sterilized by using 5.25% sodium hypochlorite solution to disinfect the system. After the sodium hypochlorite was added, all subsequent procedures were conducted in a HEPA filtered laminar flow hood to maintain asepsis.

The Optisep filter unit was assembled according to the manufacture's directions. For *E. maxima* and *E. tenella* a 10-micron Spectra/Mesh filter was used. For *E. acervulina* a 5-micron or a 10-micron filter was used. With all species the following procedures were the same.

The inlet (retentate return) and outlet tubing (permeate) were placed in a beaker containing approximately 400 ml of about 5.25% sodium hypochlorite. The pump on the filter unit was then started to flush the system with the 5.25% sodium hypochlorite. The pump was then stopped and all the valves were closed to let the system equilibrate with the 5.25% sodium hypochlorite in the chamber and tubing for about 15 minutes.

The sporulated oocyst containing vessel was then removed from refrigeration. The supernatant was pumped out without disturbing the sporulated oocyst layer. Enough supernatant was left behind so that the total solids were less than approximately 15% by volume. The sporulated oocyst suspension was then transferred to a retentate vessel.

An equal volume of about 10% sodium hypochlorite was added to the sporulated oocyst suspension to result in a final concentration of sodium hypochlorite of approximately 5% and a solids concentration of less than about 7.5% solids in suspension. The medium was mixed thoroughly and allowed to stand for about 15 minutes.

The filtration was then begun. Autoclaved water was used as the water source for filtration. The retentate pump was activated and set at 0.6 liters per minute. The permeate line was pinched closed at this time. Once air bubbles were worked through the filter membrane and tubing the permeate line was opened and directed to a collection vessel outside the laminar flow hood. The retentate flow was then increased to 2 liters per minute. A sample of the permeate was then taken and sampled for sporulated oocysts. Finding no sporulated oocysts it was determined that there was no breach of a membrane or failure of a gasket.

The volume of the retentate vessel was maintained substantially constant by the addition of either autoclaved or sterilized water. The filtration was continued until there was no chlorine odor emanating from the permeate. This required about 10 volumes of retentate to run through the system. A sample of the permeate was then analyzed for residual chlorine. The filtration was run until the permeate sample contained less than about 1 ppm of chlorine.

Once the chlorine level was sufficiently reduced, the retentate volume was then reduced by discontinuing the addition of autoclaved or sterilized water. The concentrated retentate was then aseptically transferred to a glass vessel wherein an equal volume of 1×PBS with 60 µg/ml of gentamicin was added to the disinfected sporulated oocysts suspension. This resulted in a suspension of sporulated oocysts in 0.5×PBS with approximately 30 µg/ml gentamicin. The solution was then placed in refrigeration at approximately 4° C. for future use.

Example 5

Storage

Figure 3:
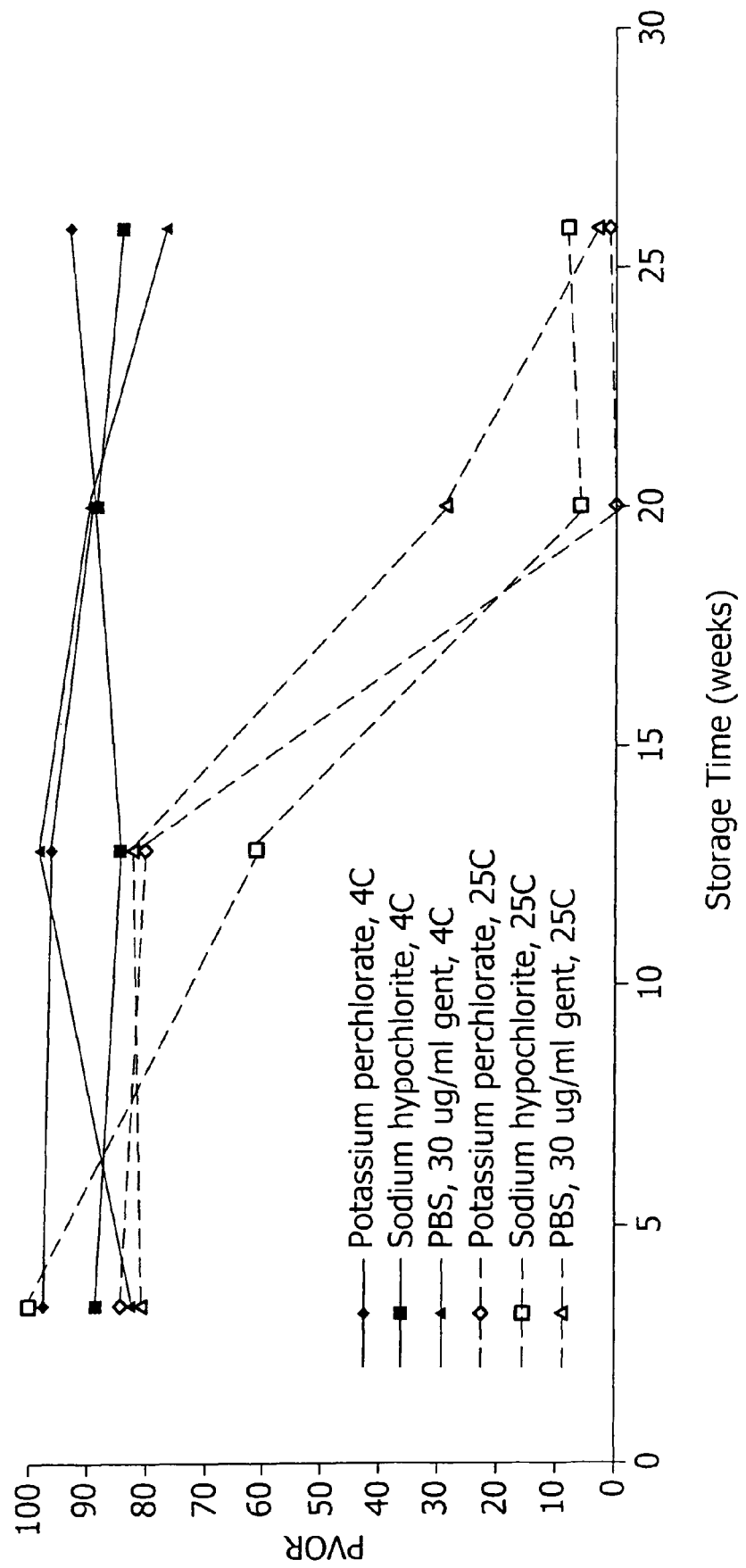
FIG. 3 shows the percent viable oocysts recovered (PVOR) versus storage time for oocytes stored under the conditions indicated. All storage medium contained *P. acnes* and oocysts were sterilized by 5% NaOCl.

Sterile sporulated oocysts were stored in 0.1% potassium perchlorate, 0.001% sodium hypochlorite, reverse osmosis/deionized (RO/DI) water or 0.5×PBS containing 30 µg/ml gentamicin and at either 4° C. or room temperature (25° C.). In some instances the storage medium also contained *Propionibacterium acnes* at a concentration of 10-100 µg/dose (dry weight). As used herein, a dose is the amount to be administered to an individual animal at one time. At the times indicated in FIGS. 3 and 4, samples were aseptically removed from the storage containers and tested for viability by vital staining.

Figure 4:
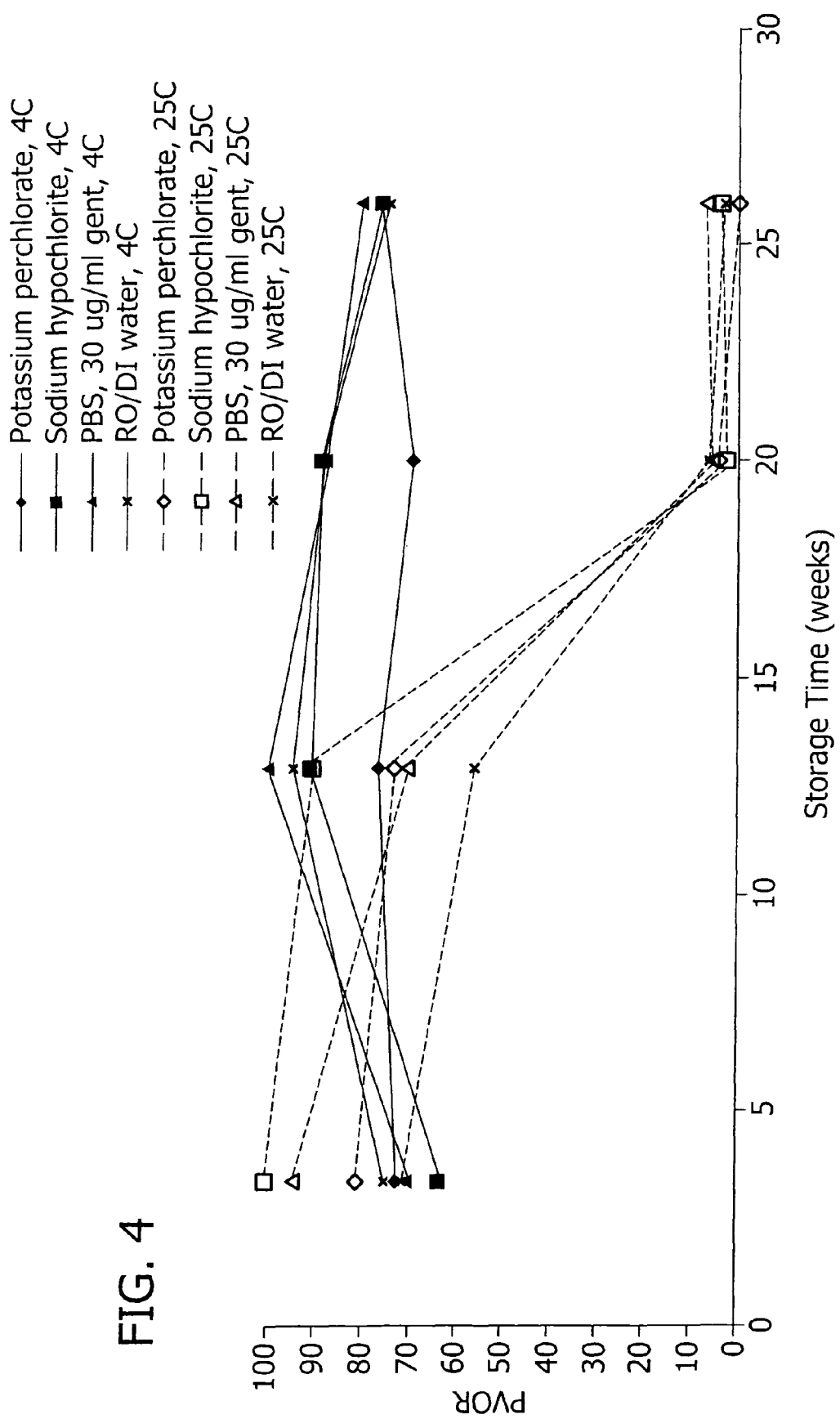
FIG. 4 shows the percent viable oocysts recovered (PVOR) versus storage time for oocytes stored under the conditions indicated. All storage medium contained *P. acnes* and oocysts were sterilized by 2% NaOCl.

The results are shown in FIGS. 4 and 5. The method of sterilization, either 2% or 5% sodium hypochlorite did not appear to have a significant effect on viability during storage. Sporulated oocysts which had not been sterilized, however, showed a rapid decrease in viability when stored.

Storage temperature was found to have an effect on ability of sporulated oocysts to remain viable during storage. Sporulated oocysts maintained at 4° C. maintained their viability for at least 26 weeks when stored in any of the medium tested. Sporulated oocysts stored at room temperature, however, showed a marked decrease in viability by 20 weeks in storage. When stored at 4° C., all groups of sporulated oocysts maintained at least 70% viability over the 26 week test period. In terms of change in percent viable oocysts recovered (PVOR), a comparison of PVOR at the first and last sampling periods shows that in no case did the decrease in PVOR exceed 10% when stored at 4° C. These results show that it is possible to maintain sporulated oocysts for extended periods of time in sterile medium lacking potassium dichromate without a significant loss in viability.

In light of the detailed description of the invention and the examples presented above, it can be appreciated that the several aspects of the invention are achieved.

It is to be understood that the present invention has been described in detail by way of illustration and example in order to acquaint others skilled in the art with the invention, its principles, and its practical application. Particular formulations and processes of the present invention are not limited to the descriptions of the specific embodiments presented, but rather the descriptions and examples should be viewed in terms of the claims that follow and their equivalents. While some of the examples and descriptions above include some conclusions about the way the invention may function, the inventors do not intend to be bound by those conclusions and functions, but put them forth only as possible explanations.

It is to be further understood that the specific embodiments of the present invention as set forth are not intended as being exhaustive or limiting of the invention, and that many alternatives, modifications, and variations will be apparent to those of ordinary skill in the art in light of the foregoing examples and detailed description. Accordingly, this invention is intended to embrace all such alternatives, modifications, and variations that fall within the spirit and scope of the following claims.

What is claimed is:

1. A method for isolating viable oocysts comprising:

collecting manure from host animals wherein said manure contains viable oocysts known to cause coccidiosis;

diluting said manure in an aqueous medium to create a slurry;

separating unwanted fecal matter from said slurry and collecting the aqueous fraction containing viable oocysts;

subjecting said aqueous fraction to separation by a hydrocyclone, and collecting the solid phase;

combining a dense aqueous liquid with said collected solid phase wherein said dense liquid has a density greater than about 1.09 g/ml and wherein the viable oocysts are buoyant;

subjecting the combination of said dense aqueous liquid and collected solid phase to centrifugation and collecting the dense liquid fraction containing viable oocysts;

diluting said dense liquid fraction to a specific gravity wherein the viable oocysts are no longer buoyant;

separating viable oocyst solids from said liquid fraction by means of a hydrocyclone and re-collecting the solid phase.

2. A method of separating viable oocysts from a liquid suspension by the use of a hydrocyclone.

3. A method as set forth in claim 2 wherein the viable oocysts are collected in the underflow from the hydrocyclone.

4. A method for isolating oocysts comprising:

collecting manure from host animals wherein said manure contains viable oocysts known to cause coccidiosis;

diluting said manure in an aqueous medium to create a slurry;

separating unwanted fecal matter from said slurry and collecting the aqueous fraction containing viable oocysts;

subjecting said aqueous fraction to separation by means of a hydrocyclone.

5. A method as set forth in claim 1 further comprising:

diluting said re-collected solid phase in an aqueous sporulation medium;

sporulating said viable oocysts while in contact with said sporulation medium;

separating sporulated oocysts from said sporulation medium;

sterilizing said sporulated oocysts; and diluting said sporulated oocysts to form a vaccine composition.

6. A method as set forth in claim 1 wherein said animals comprise the class Aves.

7. A method as set forth in claim 6 wherein said slurry is created by mixing about 0.5 gallons to about 5 gallons of domestic water per the amount of manure obtained in about 3 days from about six animals comprising the class Aves.

8. A method as set forth in claim 7 wherein said animals are chickens.

9. A method as set forth in claim 1 wherein said separation of unwanted fecal matter comprises sieving.

10. A method as set forth in claim 9 wherein said sieving is by use of multiple-tier shaker screens.

11. A method as set forth in claim 10 wherein said shaker screens comprise a 50-mesh screen and a 250-mesh screen.

12. A method as set forth in claim 1 wherein said dense aqueous liquid comprises a solution of corn syrup or sodium chloride.

13. A method as set forth in claim 1 wherein said dense aqueous liquid has a density from about 1.09 g/ml to about 1.20 g/ml.

14. A method as set forth in claim 13 wherein said dense aqueous liquid has a density from about 1.09 g/ml to about 1.14 g/ml.

15. A method as set forth in claim 14 wherein said dense aqueous liquid has a density from about 1.09 g/ml to about 1.10 g/ml.

16. The method of claim 1 wherein the dense aqueous liquid is selected from the group consisting of sucrose and fructose corn syrup.

* * * * *

UNITED STATES PATENT AND TRADEMARK OFFICE
CERTIFICATE OF CORRECTION

PATENT NO. : 7,846,685 B2
APPLICATION NO. : 10/799083
DATED : December 7, 2010
INVENTOR(S) : Jackie Green It is certified that error appears in the above-identified patent and that said Letters Patent is hereby corrected as shown below:

On the title page; item [75]; Inventors "Charles S. Schasteen, St. Louis, MO (US); Jackie Green, Lincoln, NE (US); Lance Bull, St. John, MO (US); Farooq Uraizee, Valley Park, MO (US); Mary Ann Pfannensteil, Lincoln, NE (US); Tony Allington, Valparaise, NE (US); Steven J. Mueller, Ballwin, MO (US)" should be -- Jackie Green, Lincoln, NE (US) --.

Signed and Sealed this
Twenty-sixth Day of June, 2012

David J. Kappos
*Director of the United States Patent and Trademark Office*